United States Patent
Renard et al.

(10) Patent No.: US 10,113,202 B2
(45) Date of Patent: *Oct. 30, 2018

(54) METHOD FOR DETERMINING THE METHYLATION STATUS OF THE PROMOTER REGION OF THE TWIST1 GENE IN GENOMIC DNA FROM BLADDER CELLS

(71) Applicant: MDxHealth SA, Herstal (BE)

(72) Inventors: Isabelle Renard, Sart-Tilman (BE); Wim Van Criekinge, Waarloos (BE)

(73) Assignee: MDxHealth SA, Herstal (BE)

( * ) Notice: Subject to any disclaimer, the term of this patent is extended or adjusted under 35 U.S.C. 154(b) by 0 days.

This patent is subject to a terminal disclaimer.

(21) Appl. No.: 15/079,948

(22) Filed: Mar. 24, 2016

(65) Prior Publication Data

US 2016/0208341 A1 Jul. 21, 2016

Related U.S. Application Data

(63) Continuation of application No. 12/678,696, filed as application No. PCT/EP2008/007465 on Sep. 11, 2008, now Pat. No. 9,322,065.

(60) Provisional application No. 61/071,971, filed on May 28, 2008, provisional application No. 60/960,129, filed on Sep. 17, 2007.

(51) Int. Cl.
*C12Q 1/6886* (2018.01)
*C12Q 1/68* (2018.01)

(52) U.S. Cl.
CPC ..... *C12Q 1/6886* (2013.01); *C12Q 2600/106* (2013.01); *C12Q 2600/112* (2013.01); *C12Q 2600/154* (2013.01)

(58) Field of Classification Search
CPC ............................... C12Q 1/6886; C12Q 1/68
USPC .................................. 435/6.14, 6.11, 6.1, 4
See application file for complete search history.

(56) References Cited

U.S. PATENT DOCUMENTS

| | | | |
|---|---|---|---|
| 6,410,276 B1 | 6/2002 | Burg et al. | |
| 9,322,065 B2 * | 4/2016 | Renard | C12Q 1/6886 |
| 2003/0143599 A1 | 7/2003 | Makarov et al. | |
| 2005/0239101 A1 | 10/2005 | Sukumar et al. | |
| 2007/0099209 A1 | 5/2007 | Clarke et al. | |

FOREIGN PATENT DOCUMENTS

| | | |
|---|---|---|
| JP | 2002511749 | 4/2002 |
| JP | 2002528391 | 9/2002 |
| WO | 199006995 | 6/1990 |
| WO | 199746705 | 12/1997 |
| WO | 2002061069 | 8/2002 |
| WO | 2004067726 | 8/2004 |
| WO | 2004081183 | 9/2004 |
| WO | 2004081225 | 9/2004 |
| WO | 2005042713 | 5/2005 |
| WO | 2005090507 | 9/2005 |
| WO | 2006119434 | 11/2006 |
| WO | 2007072225 | 5/2007 |
| WO | 2007116417 | 10/2007 |
| WO | 2008155549 | 12/2008 |

OTHER PUBLICATIONS

Akey et al., "Assaying DNA Methylation based on High-Throughput Melting Curve Approaches", Genomics, Oct. 2002, 80(4):376-384.
Auerkari et al., "Methylation of tumor suppressor genes p16 (INK4a), p27(Kip1) and E-cadherin in carcinogenesis", Oral Oncology, 2006, 42:5-13.
Barringer et al., "Blunt-end and single-strand ligations by *Escherichia coli* ligase: influence on an in vitro amplification scheme", Gene, 1990, 89:117-122.
Billerey et al., "Frequent FGFR3 Mutations in Papillary Non-Invasive Bladder (pTa) Tumors", American Journal of Pathology, Jun. 2001, 158(6):1955-1959.
Boyd, "The Basic Science of Oncology", McGraw-Hill, Inc. 1992, p. 379.
Compton et al., "Nucleic acid sequence-based amplification", Nature, Mar. 7, 1991, 350:91-92.
Cottrell et al., "A real-time PCR assay for DNA-methylation using methylation-specific blockers", Nucleic Acids REsearch, 2004, 32(1):e10.
Di Vinci et al., "Meth-DOP-PCR: an assay for the methylation profiling of trace amounts of DNA extracted from bodily fluids", Laboratory Investigation, 2006, 86:297-303.
Dulaimi et al., "Detection of Bladder Cancer in Urine by a Tumor Suppressor Gene Hypermethylation Panel", Clinical Cancer Research, Mar. 15, 2004, 10:1887-1893.
Eads et al., "MethyLight: a high-throughput assay to measure DNA methylation", Nucleic Acids Research, 2000, 28 (8):e32.
Entz-Werle et al., "Involvement of MET/TWIST/APC combination or the potential role of ossification factors in pediatric high-grade osteosarcoma oncogenesis", Neoplasia, Aug. 2007, 9(8):678-688.
Esteller et al., "A Gene Hypermethylation Profile of Human Cancer", Cancer Research, Apr. 15, 2001, 61:3225-3229.
Fackler et al., "DNA methylation of RASSF1A, HIN-1, RAR-beta, Cyclin D2 and Twist in in situ and invasive lobular breast carcinoma", International Journal of Cancer, 2003, 107:970-975.
Fahy et al., "Self-sustained sequence replication (3SR): an isolthermal transcription-based amplification system alternative to PCR", Genome Research, 1991, 1:25-33.

(Continued)

*Primary Examiner* — Yan Xiao
(74) *Attorney, Agent, or Firm* — Andrus Intellectual Property Law, LLP

(57) ABSTRACT

Disclosed are methods for determining the methylation status of the promoter region of the TWIST1 gene in genomic DNA from bladder cells, including bladder cells present in a urine sample. Also disclosed are kits for performing the disclosed methods, such as kits for determining the methylation status of the promoter region of the TWIST1 gene comprising at least one primer pair for determining the methylation status of TWIST1. The kits may contain means for processing a urine sample.

9 Claims, 5 Drawing Sheets

Specification includes a Sequence Listing.

(56) References Cited

OTHER PUBLICATIONS

Furuichi et al., "Chemical Modification of tRNA T yr yeast with Bisulfite: A new method to modify isopentenyladenosine residue", Biochemical and Biophysical Research Communications, 1970, 41(5):1185-1191.

Herman et al., "Methylation-specific PCR: A novel PCR assay for methylation status of CpG islands", PNAS, Sep. 1996, 93:9821-9826.

Hernandez et al., "Prospective study of FGFR3 mutations as a prognostic factor in nomuscle invasive urothelial bladder carcinomas", Journal of Clinical Oncology, Aug. 1, 2006, 24(22):3664-3671.

Hoque et al., "Quantitation of promoter methylation of multiple genes in urine DNA and bladder cancer detection", Journla of the National Cancer Institute, Jul. 19, 2006, 98(14):996-1004.

Jones et al., "The Fundamental Role of Epigenetic Events in Cancer", Nature Reviews, Genetics, Jun. 2002, 3:415-428.

Kelly et al., "Feasibility of a urine-based DNA methylation assay for early detection of bladder cancer", Methylation Profiling, Epigenetics, and Chromatin Regulation: Poster Presentations/Abstract, Sep. 17-20, 2007.

Kim et al., "RUNX3 inactivation by point mutations and aberrant DNA methylation in bladder tumors", Cancer Research, Oct. 15, 2005, 65(20):9347-9354.

Laird, "The Power and the Promise of DNA Methylation Markers", Nature Reviews: Cancer, Apr. 2003, 3:253-266.

Lotan et al., "Sensitivity and specificity of commonly available bladder tumor markers versus cytology: results of a comprehensive literature review and meta-analyses", Urology, 2003, 61:109-118.

Maruyama et al., "Abberant promoter methylation profile of bladder cancer and its relationship to clinicopatholgical features", Cancer Research, Dec. 15, 2001, 61(24):8659-8663.

Melkinov et al., "MSRE-PCR for analysis of gene-specific DNA methylation", Nucleic Acids Research, 2005, 33(10):e93.

NCBI—Gene, "TWIST1", Jun. 4, 2012.

Pritzker, "Cancer Biomarkers: Easier Said Than Done", Clinical Chemistry, 2002, 48(8):1147-1150.

Rand et al., "Conversion-specific detection of DNA methylation using real-time polymerase chain reaction (ConLight-MSP) to avoid false positives", Methods, 2002, 27:114-120.

Rein et al., "Identifying 5-methylcytosine and related modifications in DNA genomes", Nucleic Acids Research, 1998, 26(10):2255-2264.

Sasaki et al., "Bisulfite conversion-specific and methylation-specific PCR: a sensitive technique for accurate evaluation of CpG methylation", Biochemical and Biophysical Research Communications, 2003,309:305-309.

Shinozaki et al., "Distinct hypermethylation profile of primary breast cancer is associated with sentinel lymph node metastasis", Clinical Cancer Research, Mar. 15, 2005, 11(6):2156-2162.

Straub et al., "Base 5, a versatile, highly integrated high-throughput methylation profiling platform for methylation specific PCR based marker identification applied to colorectal cancer", Methylation Profiling, Epigenetics, and Chromatin Regulation: Poster Presentations/Abstract, Sep. 17-20, 2007.

Suzuki et al., "DNA methylation-associated inactivation of TGFbeta-related genes DRM/Gremlin, RUNX3, and HPP1 in human cancers", British Journal of Cancer, Oct. 31, 2005, 93(9)1029-1037.

Tockman et al., "Considerations in Bringing a Cancer Biomarker to Clinical Application", Cancer Research, May 1, 1992, 52:2711s-2718s.

Ulazzi et al., "Nidogen 1 and 2 gene promoters are aberrantly methylated in human gastrointestinal cancer", Molecular Cancer, Feb. 28, 2007, 6(1):17.

Van Oers et al., "A Simple and Fast Method for the Simultaneous Detection of Nine Fibroblast Growth Factor Receptor 3 Mutations in Bladder Cancer and Voided Urine", Clinical Cancer Research, Nov. 1, 2005, 11(21):7743-7748.

Van Rhijn et al., "Novel fibroblast growth factor receptor 3 (FGFR3) mutations in bladder cancer previously identified in non-lethal skeletal disorders", European Journal of Human Genetics, 2002, 10:819-824.

Van Rhijn et al., "Molecular Grading of Urothelial Cell Carcinoma With Fibroblast Growth Factor Receptor 3 and MIB-1 is Superior to Pathologic Grade for the Prediction of Clinical Outcome", Journal of Clinical Oncology, May 15, 2003, 21(10):1912-1921.

Wang et al., "Identification of a novel function of Twist, abHLH protein, in development of acquired taxol resistance in human cancer cells", Oncogene, Jan. 10, 2004, 23(2):474-482.

Wolff et al., "Nature Clinical Practice", Urology, Oct. 2005, 2:502-510.

Zeschnigk et al., "A novel real-time PCR assay for quantitative analysis of methylated alleles (QAMA): analysis of the retinoblastoma locus", Nucleic Acids Research, 2004, 32(16):e125.

Zhang et al., "Significance of TWIST expression and its association with E-cadherin in bladder cancer", Human Pathology, 2007, 38:598-606.

Zweig et al., "Receiver-Operating Characteristic (ROC) Plots: A Fundamental Evaluation Tool in Clinical Medicine", Clinical Chemistry, 1993, 39(4):561-577.

International Search Report and Written Opinion for PCT/EP2008/007465 dated Feb. 27, 2009.

Japanese Patent Office's Notice of Reasons for Rejection of Japanese Patent Appln. No. P2014-208231 dated Jul. 5, 2016.

Translation of Japanese Patent Office's Reasons for Rejection of Japanese Patent Appln. No. P2014-208231 dated Jul. 5, 2016.

Boyd (The Basic Science of Oncology, 1992, McGraw-Hill, Inc., p. 379).

Pritzker (Clinical Chemistry, 2002, 48:1147-1150).

Tockman et al. (Cancer Res., 1992, 52:2711s-2718s).

Wolff et al. (Nature Clinical Practice: Urology, 2005, 2: 502-510, hereafter, Wolff).

NCBI-Gene-TWIST1 on Jun. 4, 2012.

Renard et al., "Feasibility of a urine-based DNA methylation assay for early detection of bladder cancer", Methylation Profiling, Epigenetics, and Chromatin Regulation: Poster Presentations/Abstract, Sep. 17-20, 2007.

Joseph J. Fantony, et al. "It May Be Time to Abandon Urine Tests for Bladder Cancer", JNCCN, vol. 13, No. 9, Sep. 2015, pp. 1163-1166.

Zheng Zhang, et al. "Significance of TWIST expression and its association with E-cadherin in bladder cancer", Human Pathology (2007) 38, 598-606.

* cited by examiner

SEQUENCE LISTING

```
<160> NUMBER OF SEQ ID NOS: 56

<210> SEQ ID NO 1
<211> LENGTH: 18
<212> TYPE: DNA
<213> ORGANISM: Artificial
<220> FEATURE:
<223> OTHER INFORMATION: Primer

<400> SEQUENCE: 1
gcgttgaagt cggggttc                                                 18

<210> SEQ ID NO 2
<211> LENGTH: 24
<212> TYPE: DNA
<213> ORGANISM: Artificial
<220> FEATURE:
<223> OTHER INFORMATION: Primer

<400> SEQUENCE: 2
cccgtacttc gctaacttta aacg                                          24

<210> SEQ ID NO 3
<211> LENGTH: 42
<212> TYPE: DNA
<213> ORGANISM: Artificial
<220> FEATURE:
<223> OTHER INFORMATION: Molecular Beacon Probe

<400> SEQUENCE: 3
cgtctgcgtg gtttcgttcg gttcgcgttt gttaggcaga cg                      42

<210> SEQ ID NO 4
<211> LENGTH: 18
```

```
<212> TYPE: DNA
<213> ORGANISM: Artificial
<220> FEATURE:
<223> OTHER INFORMATION: Primer

<400> SEQUENCE: 4
tattgcggag tgcgggtc                                              18

<210> SEQ ID NO 5
<211> LENGTH: 18
<212> TYPE: DNA
<213> ORGANISM: Artificial
<220> FEATURE:
<223> OTHER INFORMATION: Primer

<400> SEQUENCE: 5
tcgacgaact cccgacga                                              18

<210> SEQ ID NO 6
<211> LENGTH: 48
<212> TYPE: DNA
<213> ORGANISM: Artificial
<220> FEATURE:
<223> OTHER INFORMATION: Molecular Beacon Probe

<400> SEQUENCE: 6
cgacatgcgt tgtgtaattc gttggatgcg gattagggcg gcatgtcg             48

<210> SEQ ID NO 7
<211> LENGTH: 19
<212> TYPE: DNA
<213> ORGANISM: Artificial
<220> FEATURE:
<223> OTHER INFORMATION: Primer

<400> SEQUENCE: 7
gttatggcga tgcggtttc                                             19

<210> SEQ ID NO 8
<211> LENGTH: 20
<212> TYPE: DNA
<213> ORGANISM: Artificial
<220> FEATURE:
<223> OTHER INFORMATION: Primer

<400> SEQUENCE: 8
ccaacctaaa aaacgaccga                                            20

<210> SEQ ID NO 9
<211> LENGTH: 36
<212> TYPE: DNA
<213> ORGANISM: Artificial
<220> FEATURE:
<223> OTHER INFORMATION: Molecular Beacon Probe

<400> SEQUENCE: 9
cgacatgcac gacgccccg aacctaacgc atgtcg                           36

<210> SEQ ID NO 10
<211> LENGTH: 21
<212> TYPE: DNA
<213> ORGANISM: Artificial
<220> FEATURE:
<223> OTHER INFORMATION: Primer

<400> SEQUENCE: 10
```
gtcgtcgaga agggttcgtt t                                              21

<210> SEQ ID NO 11
<211> LENGTH: 24
<212> TYPE: DNA
<213> ORGANISM: Artificial
<220> FEATURE:
<223> OTHER INFORMATION: Primer

<400> SEQUENCE: 11
gcgtattcta cttaacctat ccgc                                           24

<210> SEQ ID NO 12
<211> LENGTH: 37
<212> TYPE: DNA
<213> ORGANISM: Artificial
<220> FEATURE:
<223> OTHER INFORMATION: Molecular Beacon Probe

<400> SEQUENCE: 12
cgacatgcac gaccccgcct cccccgccg catgtcg                              37

<210> SEQ ID NO 13
<211> LENGTH: 23
<212> TYPE: DNA
<213> ORGANISM: Artificial
<220> FEATURE:
<223> OTHER INFORMATION: Primer

<400> SEQUENCE: 13
taaattagat cgtcgtttcg gag                                            23

<210> SEQ ID NO 14
<211> LENGTH: 21
<212> TYPE: DNA
<213> ORGANISM: Artificial
<220> FEATURE:
<223> OTHER INFORMATION: Primer

<400> SEQUENCE: 14
tacctcaatt tctcgatccg c                                              21

<210> SEQ ID NO 15
<211> LENGTH: 43
<212> TYPE: DNA
<213> ORGANISM: Artificial
<220> FEATURE:
<223> OTHER INFORMATION: Molecular Beacon Probe

<400> SEQUENCE: 15
cgacatgctg ggagggttcg cggttattgt aaggagcatg tcg                      43

<210> SEQ ID NO 16
<211> LENGTH: 21
<212> TYPE: DNA
<213> ORGANISM: Artificial
<220> FEATURE:
<223> OTHER INFORMATION: Primer

<400> SEQUENCE: 16
gttagagcgc gtttttagcg t                                              21

<210> SEQ ID NO 17
<211> LENGTH: 21
<212> TYPE: DNA
<213> ORGANISM: Artificial

```
<220> FEATURE:
<223> OTHER INFORMATION: Primer

<400> SEQUENCE: 17
ccgcaatacc taacacttcc g                                              21

<210> SEQ ID NO 18
<211> LENGTH: 37
<212> TYPE: DNA
<213> ORGANISM: Artificial
<220> FEATURE:
<223> OTHER INFORMATION: Molecular Beacon Probe

<400> SEQUENCE: 18
cgacatgccc gacacgctcc gaaacaccag catgtcg                             37

<210> SEQ ID NO 19
<211> LENGTH: 24
<212> TYPE: DNA
<213> ORGANISM: Artificial
<220> FEATURE:
<223> OTHER INFORMATION: Primer

<400> SEQUENCE: 19
gtgttaagag tgcgtagtaa gacg                                           24

<210> SEQ ID NO 20
<211> LENGTH: 21
<212> TYPE: DNA
<213> ORGANISM: Artificial
<220> FEATURE:
<223> OTHER INFORMATION: Primer

<400> SEQUENCE: 20
gaaacgaacg tacaaaaacg a                                              21

<210> SEQ ID NO 21
<211> LENGTH: 47
<212> TYPE: DNA
<213> ORGANISM: Artificial
<220> FEATURE:
<223> OTHER INFORMATION: Molecular Beacon Probe

<400> SEQUENCE: 21
cgacatgccg aaactataaa tcaactacga aacaaacgcg catgtcg                  47

<210> SEQ ID NO 22
<211> LENGTH: 22
<212> TYPE: DNA
<213> ORGANISM: Artificial
<220> FEATURE:
<223> OTHER INFORMATION: Primer

<400> SEQUENCE: 22
gttagggttc ggggcgttg tt                                              22

<210> SEQ ID NO 23
<211> LENGTH: 21
<212> TYPE: DNA
<213> ORGANISM: Artificial
<220> FEATURE:
<223> OTHER INFORMATION: Primer

<400> SEQUENCE: 23
ccgtcgcctt cctccgacga a                                              21
```

```
<210> SEQ ID NO 24
<211> LENGTH: 38
<212> TYPE: DNA
<213> ORGANISM: Artificial
<220> FEATURE:
<223> OTHER INFORMATION: Molecular Beacon Probe

<400> SEQUENCE: 24
cgacatgccg gcggggaagg aaatcgtttc gcatgtcg                          38

<210> SEQ ID NO 25
<211> LENGTH: 21
<212> TYPE: DNA
<213> ORGANISM: Artificial
<220> FEATURE:
<223> OTHER INFORMATION: Primer

<400> SEQUENCE: 25
tagagtacgt gtcggtcgga t                                           21

<210> SEQ ID NO 26
<211> LENGTH: 21
<212> TYPE: DNA
<213> ORGANISM: Artificial
<220> FEATURE:
<223> OTHER INFORMATION: Primer

<400> SEQUENCE: 26
acaaaaacaa aaacgacgcc t                                           21

<210> SEQ ID NO 27
<211> LENGTH: 36
<212> TYPE: DNA
<213> ORGANISM: Artificial
<220> FEATURE:
<223> OTHER INFORMATION: Molecular Beacon Probe

<400> SEQUENCE: 27
cgacatgccg ggtgttgttg gtcggcgcgc atgtcg                            36

<210> SEQ ID NO 28
<211> LENGTH: 21
<212> TYPE: DNA
<213> ORGANISM: Artificial
<220> FEATURE:
<223> OTHER INFORMATION: Primer

<400> SEQUENCE: 28
gagatcgcgg gttttttattt c                                          21

<210> SEQ ID NO 29
<211> LENGTH: 19
<212> TYPE: DNA
<213> ORGANISM: Artificial
<220> FEATURE:
<223> OTHER INFORMATION: Primer

<400> SEQUENCE: 29
ccaacttcct acgacgcat                                              19

<210> SEQ ID NO 30
<211> LENGTH: 36
<212> TYPE: DNA
<213> ORGANISM: Artificial
<220> FEATURE:
<223> OTHER INFORMATION: Molecular Beacon Probe
```

```
<400> SEQUENCE: 30
cgacatgcct cccaaccgcg cgacacaagc atgtcg                              36

<210> SEQ ID NO 31
<211> LENGTH: 21
<212> TYPE: DNA
<213> ORGANISM: Artificial
<220> FEATURE:
<223> OTHER INFORMATION: Primer

<400> SEQUENCE: 31
cgtagggttg tatttgagcg a                                             21

<210> SEQ ID NO 32
<211> LENGTH: 23
<212> TYPE: DNA
<213> ORGANISM: Artificial
<220> FEATURE:
<223> OTHER INFORMATION: Primer

<400> SEQUENCE: 32
taacttttaa cgaaattacc ccg                                           23

<210> SEQ ID NO 33
<211> LENGTH: 47
<212> TYPE: DNA
<213> ORGANISM: Artificial
<220> FEATURE:
<223> OTHER INFORMATION: Molecular Beacon Probe

<400> SEQUENCE: 33
cgacatgccg ggttaggggg gcgtaaaatt ttattcgttg catgtcg                  47

<210> SEQ ID NO 34
<211> LENGTH: 22
<212> TYPE: DNA
<213> ORGANISM: Artificial
<220> FEATURE:
<223> OTHER INFORMATION: Primer

<400> SEQUENCE: 34
ggcgtttagg ttaattttc gt                                             22

<210> SEQ ID NO 35
<211> LENGTH: 21
<212> TYPE: DNA
<213> ORGANISM: Artificial
<220> FEATURE:
<223> OTHER INFORMATION: Primer

<400> SEQUENCE: 35
cgatcccata tctaaaaccg a                                             21

<210> SEQ ID NO 36
<211> LENGTH: 35
<212> TYPE: DNA
<213> ORGANISM: Artificial
<220> FEATURE:
<223> OTHER INFORMATION: Molecular Beacon Probe

<400> SEQUENCE: 36
cgacatgcct cgcgatccgc ccgaaacgca tgtcg                              35

<210> SEQ ID NO 37
```

```
<211> LENGTH: 23
<212> TYPE: DNA
<213> ORGANISM: Artificial
<220> FEATURE:
<223> OTHER INFORMATION: Primer

<400> SEQUENCE: 37
agcgtagaga taggttggta acg                                            23

<210> SEQ ID NO 38
<211> LENGTH: 22
<212> TYPE: DNA
<213> ORGANISM: Artificial
<220> FEATURE:
<223> OTHER INFORMATION: Primer

<400> SEQUENCE: 38
aaaacgataa cccttaaacc ga                                             22

<210> SEQ ID NO 39
<211> LENGTH: 36
<212> TYPE: DNA
<213> ORGANISM: Artificial
<220> FEATURE:
<223> OTHER INFORMATION: Molecular Beacon Probe

<400> SEQUENCE: 39
cgacatgcgc ggaggggtta gcgtggttgc atgtcg                              36

<210> SEQ ID NO 40
<211> LENGTH: 25
<212> TYPE: DNA
<213> ORGANISM: Artificial
<220> FEATURE:
<223> OTHER INFORMATION: Primer

<400> SEQUENCE: 40
gcggttttta aggagtttta ttttc                                          25

<210> SEQ ID NO 41
<211> LENGTH: 21
<212> TYPE: DNA
<213> ORGANISM: Artificial
<220> FEATURE:
<223> OTHER INFORMATION: Primer

<400> SEQUENCE: 41
ctacgaaatt ccctttacgc t                                              21

<210> SEQ ID NO 42
<211> LENGTH: 39
<212> TYPE: DNA
<213> ORGANISM: Artificial
<220> FEATURE:
<223> OTHER INFORMATION: Molecular Beacon Probe

<400> SEQUENCE: 42
cgacatgggt tcgtaaggtt tggggtagcg gccatgtcg                           39

<210> SEQ ID NO 43
<211> LENGTH: 21
<212> TYPE: DNA
<213> ORGANISM: Artificial
<220> FEATURE:
<223> OTHER INFORMATION: Primer

<400> SEQUENCE: 43
```

```
gcgttaaggt acgggttttt c                                              21

<210> SEQ ID NO 44
<211> LENGTH: 19
<212> TYPE: DNA
<213> ORGANISM: Artificial
<220> FEATURE:
<223> OTHER INFORMATION: Primer

<400> SEQUENCE: 44
gccatttcgc ctaacgaac                                                 19

<210> SEQ ID NO 45
<211> LENGTH: 35
<212> TYPE: DNA
<213> ORGANISM: Artificial
<220> FEATURE:
<223> OTHER INFORMATION: Molecular Beacon Probe

<400> SEQUENCE: 45
cgacatgcac gcgccctcct tcgacacgca tgtcg                               35

<210> SEQ ID NO 46
<211> LENGTH: 26
<212> TYPE: DNA
<213> ORGANISM: Artificial
<220> FEATURE:
<223> OTHER INFORMATION: Primer

<400> SEQUENCE: 46
tagggagtat ataggttggg gaagtt                                         26

<210> SEQ ID NO 47
<211> LENGTH: 27
<212> TYPE: DNA
<213> ORGANISM: Artificial
<220> FEATURE:
<223> OTHER INFORMATION: Primer

<400> SEQUENCE: 47
aacacacaat aacaaacaca aattcac                                        27

<210> SEQ ID NO 48
<211> LENGTH: 42
<212> TYPE: DNA
<213> ORGANISM: Artificial
<220> FEATURE:
<223> OTHER INFORMATION: Molecular Beacon Probe

<400> SEQUENCE: 48
cgactgcgtg tggggtggtg atggaggagg tttaggcagt cg                       42

<210> SEQ ID NO 49
<211> LENGTH: 66
<212> TYPE: DNA
<213> ORGANISM: Artificial
<220> FEATURE:
<223> OTHER INFORMATION: Primer

<400> SEQUENCE: 49
tttttttttt tttttttttt tttttttttt tttttttttt ttttttcgtc atctgccccc    60
acagag                                                               66

<210> SEQ ID NO 50
```

```
<211> LENGTH: 55
<212> TYPE: DNA
<213> ORGANISM: Artificial
<220> FEATURE:
<223> OTHER INFORMATION: Primer

<400> SEQUENCE: 50
tttttttttt tttttttttt tttttttttt ttttttttctg ccccacaga gcgct         55

<210> SEQ ID NO 51
<211> LENGTH: 47
<212> TYPE: DNA
<213> ORGANISM: Artificial
<220> FEATURE:
<223> OTHER INFORMATION: Primer

<400> SEQUENCE: 51
tttttttttt tttttttttt tttttttttc tgccccaca gagcgct                   47

<210> SEQ ID NO 52
<211> LENGTH: 48
<212> TYPE: DNA
<213> ORGANISM: Artificial
<220> FEATURE:
<223> OTHER INFORMATION: Primer

<400> SEQUENCE: 52
tttttttttt tttttttttt ttttttttg gtggaggctg acgaggcg                  48

<210> SEQ ID NO 53
<211> LENGTH: 61
<212> TYPE: DNA
<213> ORGANISM: Artificial
<220> FEATURE:
<223> OTHER INFORMATION: Primer

<400> SEQUENCE: 53
tttttttttt tttttttttt tttttttttt tttttttttt tttacgaggc gggcagtgtg    60
t                                                                    61

<210> SEQ ID NO 54
<211> LENGTH: 54
<212> TYPE: DNA
<213> ORGANISM: Artificial
<220> FEATURE:
<223> OTHER INFORMATION: Primer

<400> SEQUENCE: 54
tttttttttt tttttttttt tttttttttt ttttcctgtt catcctggtg gtgg          54

<210> SEQ ID NO 55
<211> LENGTH: 72
<212> TYPE: DNA
<213> ORGANISM: Artificial
<220> FEATURE:
<223> OTHER INFORMATION: Primer

<400> SEQUENCE: 55
tttttttttt tttttttttt tttttttttt tttttttttt tttttttttt gcacaacctc    60
gactactaca ag                                                        72

<210> SEQ ID NO 56
<211> LENGTH: 42
<212> TYPE: DNA
<213> ORGANISM: Artificial
```

```
<220> FEATURE:
<223> OTHER INFORMATION: Primer

<400> SEQUENCE: 56
tttttttttt tttttttttt cacaacctcg actactacaa ga                    42
```

METHOD FOR DETERMINING THE METHYLATION STATUS OF THE PROMOTER REGION OF THE TWIST1 GENE IN GENOMIC DNA FROM BLADDER CELLS

CROSS-REFERENCE TO RELATED APPLICATIONS

This application is a continuation of U.S. application Ser. No. 12/678,696, filed on Jun. 16, 2010, which application was published on Nov. 4, 2010, as US2010/0280134, and further is the U.S. national stage application of International Application No. PCT/EP2008/007465, filed on Sep. 11, 2008, which international application was published on Mar. 26, 2009, as WO2009/036922 in the English language. The International Application No. PCT/EP2008/007465 claims priority of U.S. Provisional Patent Application No. 61/071,971, filed on May 28, 2008, and U.S. Provisional Patent Application No. 60/960,129, filed on Sep. 17, 2007; and International Application No. PCT/GB2008/002093, filed on Jun. 19, 2008.

FIELD OF THE INVENTION

The present invention relates to methods and kits for detecting the presence of cancer cells, or the presence of genomic DNA from cancer cells, which include determining the methylation status, or the expression levels, or a combination thereof, of a panel of genes. In particular the invention relates to the detection of bladder cancer. The invention also relates to pharmacogenetic methods for determining suitable treatment regimens for cancer and methods for treating cancer patients.

BACKGROUND OF THE INVENTION

Molecular evidence supports the concept that cancer is a stepwise process of accumulation of genetic and epigenetic abnormalities that can lead to abnormal gene silencing or gene activation and cellular dysfunction. Synergy between genetic and epigenetic processes drives tumor progression and malignancy.

Epigenetics can be described as a stable alteration in gene expression potential that takes place during development and cell proliferation, mediated by mechanisms other than alterations in the primary nucleotide sequence of a gene. Three related mechanisms that cause epigenetic alteration in gene expression are DNA methylation, histone code changes and RNA interference.

DNA methylation is the main epigenetic modification in humans. It is a chemical modification of DNA performed by enzymes called methyltransferases, in which a methyl group (m) is added to specific cytosine (C) residues in DNA. In mammals, methylation occurs only at cytosine residues adjacent to a guanosine residue, i.e. at the sequence CG or at the CpG dinucleotide. In normal cells, methylation occurs predominantly in regions of DNA that have few CG base repeats, while CpG islands, regions of DNA that have long repeats of CG bases, remain non-methylated. Gene promoter regions that control protein expression are often CpG island-rich. Aberrant methylation of these normally non-methylated CpG islands in the promoter region causes transcriptional inactivation or silencing of certain functional genes in human cancers (Jones 2002).

Diagnostic markers for cancer detection have been described. One can distinguish between immunological markers and genetic markers. Genetic markers are based on detection of mutation in distinct genes, in particular in tumor suppressor genes. More recently, DNA methylation markers have been evaluated as potential genetic markers for detection of cancer because they offer certain advantages when compared to mutation markers. One of the most important features is that they occur at the early stages of cancer development and in many cases are tissue- and tumor-type specific (Esteller et al. 2001). A further advantage is that the methylation profile is preserved in purified isolated DNA and methylation changes appear to precede apparent malignancy in many cases. In addition, methylation markers may serve predictive purposes as they often reflect the sensitivity to therapy or duration of patient survival. All of these features find their application in improved cancer detection and therapy.

An early diagnosis is critical for the successful treatment of many types of cancer. The traditional methods of diagnosis (such as cytology, histopathology, immunohistochemistry, serology, and so on) are useful, but molecular markers can further subclassify the tumors and identify predisposition to cancer. If the exact methylation profiles of tumors are available and drugs targeting the specific genes are obtainable, then the treatment of cancer could be more focused and rational. Therefore, the detection and mapping of novel methylation markers is an essential step towards improvement of cancer prevention, screening and treatment.

Each year in the U.S. and EU, bladder cancer is diagnosed in >160,000 men and results in >48,000 deaths. While the five-year survival rate for early-stage bladder cancer is high, over 25% present with advanced disease and around 70% experience recurrence or progression following treatment. Urine cytology and cystoscopy are the current standard-of-care for bladder cancer detection and surveillance. Cystoscopy is highly sensitive but is invasive, expensive and causes significant patient discomfort. Urinary cytology is the most widely used method for non-invasive detection with up to 100% specificity. Unfortunately, this method is limited by its sensitivity, which is especially poor for low-grade bladder tumours.

Several methods have been reported for the detection of tumour cells in voided urine. However, none of these urinary tests can replace cystoscopy due to their poor specificity. Combining different methods of bladder cancer detection has been shown to improve sensitivity but unfortunately at the expense of specificity (Lotan Y et al., 2003).

Activating mutations in the fibroblast growth factor receptor 3 (FGFR3) gene have been reported in >50% of primary bladder tumors (van Rhijn B W G et al., 2003). Most of the somatic mutations found in bladder cancer are identical to germ line mutations responsible for skeletal disorders such as thanatophoric dysplasia and achondroplasia (van Rhijn B W G et al., 2002). It has been reported that FGFR3 mutations are very frequent in bladder tumors of low stage and grade, indicating that they occur much more frequently in superficial bladder cancer than in invasive bladder cancer (Billerey C et al., 2001). Recently the development of a new method for FGFR3 mutation analysis based on the detection of single nucleotide changes has been described by van Oers et al. With this method, the nine most common mutations can be detected in one assay simultaneously.

Ulazzi et al (Molecular Cancer 2007, 6:17) describe methylation of nidogen genes in colon and gastric cancer cell lines.

BRIEF DESCRIPTION OF THE INVENTION

The invention, as set out in the claims, is based around the discovery of specific genes and panels of genes whose methylation status is linked to predisposition to, or the incidence of bladder cancer. Use of these genes for detecting bladder cancer, in particular in the context of appropriate tissue or urine samples, has been shown to produce highly sensitive and specific results.

Accordingly, the invention provides a method of detecting a predisposition to, or the incidence of, bladder cancer in a sample comprising detecting an epigenetic change in at least one gene selected from NID2, TJP2, TWIST1, TNFRSF25, BMP7, RUNX3, CCNA1, APC, LOXL1, TUBB4, NTRK2, ARFGAP3, PDLIM4, RASSF1A and OSMR, wherein detection of the epigenetic change is indicative of a predisposition to, or the incidence of, bladder cancer.

The most preferred epigenetic change in the at least one gene selected from NID2, TJP2, TWIST1, TNFRSF25, BMP7, RUNX3, CCNA1, APC, LOXL1, TUBB4, NTRK2, ARFGAP3, PDLIM4, RASSF1A and OSMR, which is detected comprises, consists essentially of or consists of methylation. In particular, aberrant methylation, which may be referred to as hypermethylation, of the gene or genes is detected.

Thus, the invention provides preferably for a method of detecting a predisposition to, or the incidence of, bladder cancer in a sample comprising detecting epigenetic silencing in at least one gene selected from NID2, TJP2, TWIST1, TNFRSF25, BMP7, RUNX3, CCNA1, APC, LOXL1, TUBB4, NTRK2, ARFGAP3, PDLIM4, RASSF1A and OSMR, wherein epigenetic silencing of the at least one gene is detected by determination of the methylation status of the gene and wherein methylation of the gene is indicative of a predisposition to, or the incidence of, bladder cancer.

Methylation changes that develop early in the process of carcinogenesis are not only ideal for screening purposes, but also interesting targets for monitoring staging. Accordingly, the invention also provides for a method for determining the histopathological stage of bladder cancer in a sample comprising detecting an epigenetic change in at least one gene selected from NID2, TJP2, TWIST1, TNFRSF25, BMP7, RUNX3, CCNA1, APC, LOXL1, TUBB4, NTRK2, ARFGAP3, PDLIM4, RASSF1A and OSMR, wherein detection of the epigenetic change is indicative of the histopathological stage of the bladder cancer.

Epigenetic loss of gene function can be rescued by the use of DNA demethylating agents and/or DNA methyltransferase inhibitors and/or HDAC inhibitor. In one aspect, the invention provides for a method for predicting the likelihood of successful treatment of bladder cancer with a DNA demethylating agent and/or a DNA methyltransferase inhibitor and/or HDAC inhibitor comprising detecting an epigenetic change in at least one gene selected from NID2, TJP2, TWIST1, TNFRSF25, BMP7, RUNX3, CCNA1, APC, LOXL1, TUBB4, NTRK2, ARFGAP3, PDLIM4, RASSF1A and OSMR, wherein detection of the epigenetic change is indicative that the likelihood of successful treatment is higher than if the epigenetic modification is not detected.

In an opposite scenario, the invention provides for a method for predicting the likelihood of resistance to treatment of bladder cancer with a DNA demethylating agent and/or DNA methyltransferase inhibitor and/or HDAC inhibitor comprising detecting an epigenetic change in at least one gene selected from NID2, TJP2, TWIST1, TNFRSF25, BMP7, RUNX3, CCNA1, APC, LOXL1, TUBB4, NTRK2, ARFGAP3, PDLIM4, RASSF1A and OSMR, wherein detection of the epigenetic change is indicative that the likelihood of resistance to treatment is lower than if the epigenetic modification is not detected.

Bladder cancer is defined to include transitional cell carcinoma or squamous cell carcinomas. Epigenetic loss of gene function can identify the need for treatment which may differ according to the type of carcinoma. Therefore, the present invention also relates to a method of selecting a suitable treatment regimen for bladder cancer comprising detecting an epigenetic change in at least one gene selected from NID2, TJP2, TWIST1, TNFRSF25, BMP7, RUNX3, CCNA1, APC, LOXL1, TUBB4, NTRK2, ARFGAP3, PDLIM4, RASSF1A and OSMR, wherein detection of the epigenetic change results in selection of a DNA demethylating agent and/or a DNA methyltransferase inhibitor and/or a HDAC inhibitor for treatment and wherein if the epigenetic change is not detected, a DNA demethylating agent and/or a DNA methyltransferase inhibitor and/or a HDAC inhibitor is not selected for treatment.

In a related aspect, the invention provides for a method for predicting suitable treatment of a transitional cell carcinoma or squamous cell carcinoma comprising (in a sample obtained from a subject), determining the methylation status of at least one gene selected from NID2, TJP2, TWIST1, TNFRSF25, BMP7, RUNX3, CCNA1, APC, LOXL1, TUBB4, NTRK2, ARFGAP3, PDLIM4, RASSF1A and OSMR, in a transitional cell tumor or squamous cell carcinoma, wherein if the at least one gene is methylated, in particular hypermethylated, the need of resection of the transitional cell carcinoma or squamous cell carcinoma is identified.

In an opposite scenario, the invention provides for a method for predicting suitable treatment of a transitional cell carcinoma or squamous cell carcinoma comprising (in a sample obtained from a subject), determining the methylation status at least one gene selected from NID2, TJP2, TWIST1, TNFRSF25, BMP7, RUNX3, CCNA1, APC, LOXL1, TUBB4, NTRK2, ARFGAP3, PDLIM4, RASSF1A and OSMR, in a transitional cell tumor or squamous cell carcinoma, wherein if the at least one gene is unmethylated or methylated to a lesser degree, it is decided that there is no need for resection of the transitional cell or squamous cell tumor.

In a further related aspect, the invention provides for a method of treating bladder cancer in a subject comprising administration of a DNA demethylating agent and/or a DNA methyltransferase inhibitor wherein the subject has been selected for treatment on the basis of a method of the invention.

The invention also relates to a kit for detecting a predisposition to, or the incidence of, bladder cancer in a sample comprising:
(a) means for detecting an epigenetic change in at least one gene selected from NID2, TJP2, TWIST1, TNFRSF25, BMP7, RUNX3, CCNA1, APC, LOXL1, TUBB4, NTRK2, ARFGAP3, PDLIM4, RASSF1A and OSMR
(b) means for processing a urine sample.

The invention also provides a kit for detecting a predisposition to, or the incidence of, bladder cancer in a sample comprising at least one primer pair for determining the methylation status of each of NID2, TWIST1 and RUNX3.

The invention further provides for primers and/or probes for carrying out the methods of the invention as described herein, including variants thereof.

DETAILED DESCRIPTION OF THE INVENTION

The present invention is based on the discovery that cytosines within CpG dinucleotides in at least one gene selected from NID2, TJP2, TWIST1, TNFRSF25, BMP7, RUNX3, CCNA1, APC, LOXL1, TUBB4, NTRK2, ARF-GAP3, PDLIM4, RASSF1A and OSMR are differentially methylated in human tissue cancer/urine samples and unmethylated in normal human tissue/urine samples, more in particular in bladder tissue and/or urine samples.

The invention provides in a first aspect a method of detecting a predisposition to, or the incidence of, bladder cancer in a sample comprising detecting an epigenetic change in at least one gene selected from NID2, TJP2, TWIST1, TNFRSF25, BMP7, RUNX3, CCNA1, APC, LOXL1, TUBB4, NTRK2, ARFGAP3, PDLIM4, RASSF1A and OSMR, wherein detection of the epigenetic change is indicative of a predisposition to, or the incidence of, bladder cancer. A particularly useful marker which may be utilised in isolation or as part of a panel of genes is TWIST1. This gene has been shown for the first time herein to permit detection of bladder cancer with high levels of specificity and sensitivity.

Preferably, the invention involves detecting an epigenetic change in a panel of genes comprising at least two, three, four or five of the genes from NID2, TJP2, TWIST1, TNFRSF25, BMP7, RUNX3, CCNA1, APC, LOXL1, TUBB4, NTRK2, ARFGAP3, PDLIM4, RASSF1A and OSMR, wherein detection of an epigenetic change in at least one of the genes in the panel is indicative of a predisposition to, or the incidence of, bladder cancer. Preferably, an epigenetic change in at least two, three, four or five genes from NID2, TJP2, TWIST1, TNFRSF25, BMP7, RUNX3, CCNA1, APC, LOXL1, TUBB4, NTRK2, ARFGAP3, PDLIM4, RASSF1A and OSMR is detected. The panel of genes preferably comprises TWIST1. The panel of genes may additionally or alternatively comprise NID2 and/or BMP7. The panel of genes may comprise TWIST1 and/or NID2 and/or BMP7 and/or RUNX3.

In certain embodiments the panel of genes comprises, consists essentially of or consists of NID2, TWIST1 and RUNX3. This three gene panel has been shown for the first time herein to permit detection of bladder cancer with high levels of specificity and sensitivity. Specifically, detection of methylation of at least one of the three genes gives a reliable indicator of bladder cancer in suitable genomic DNA containing samples, such as urine samples. The panel of genes may comprise, consist essentially of or consist of NID2 and BMP7, NID2, TJP2 and BMP7, NID2, TNFRSF25 and BMP7 or NID2, BMP7, TWIST1, CCNA1 and RUNX3. The detection of an epigenetic change in each of the panel of genes may be carried out in a single reaction.

"NID2, TJP2, TWIST1, TNFRSF25, BMP7, RUNX3, CCNA1, APC, LOXL1, TUBB4, NTRK2, ARFGAP3, PDLIM4, RASSF1A and OSMR" is the standard nomenclature for "NID2" nidogen 2 (Accession number: AB009799 and ENSG0000008703), "TJP2" tight junction protein 2 (Accession number: NM_0004817), "TWIST1" twist homolog 1 (Accession number: NM_000474), "TNFRSF25" tumor necrosis factor receptor superfamily, member 25 (Accession number: NM_148972), "BMP7" bone morphogenetic protein 7 (Accession number: ENSG000000101144), "RUNX3" runt-related transcription factor 3 (Accession number: ENST00000308873), "CCNA1" cyclin A1 (Accession number: NM_003914), "APC" adenomatosis polyposis coli (Accession number: NM_000038), "LOXL1" lysyl oxidase-like 1 (Accession number: ENST00000261921), "TUBB4" tubulin, beta 4 (Accession number: NM_006087), "NTRK2" neurotrophic tyrosine kinase, receptor, type 2 (Accession number: NM_001007097), "ARFGAP3" ADP-ribosylation factor GTPase activating protein 3 (Accession number: AK002083 and ENSG00000100262), "PDLIM4" PDZ and LIM domain 4 (Accession number: ENST00000379038 NM_001719), "RASSF1A" Ras association (RalGDS/AF-6) domain family 1 (Accession number: AC002481), and "OSMR" oncostatin M receptor (Accession number: NM_003999), as approved by the Human Genome Organisation. FGFR3 is the approved nomenclature for fibroblast growth factor receptor 3 (located on chromosome 4p16.3, accession M64347).

By "gene" is meant any gene which is taken from the family to which the named "gene" belongs and includes according to all aspects of the invention not only the particular sequences found in the publicly available database entries, but also encompasses transcript and nucleotide variants of these sequences, with the proviso that methylation or another epigenetic modification of the gene is linked to bladder cancer.

The methods of the invention are preferably ex vivo or in vitro methods carried out on a test sample. The methods are non-invasive. The methods may be used to identify any type of cancer, in particular bladder cancer.

The "test sample" to detect epigenetic silencing of the at least one gene selected from NID2, TJP2, TWIST1, TNFRSF25, BMP7, RUNX3, CCNA1, APC, LOXL1, TUBB4, NTRK2, ARFGAP3, PDLIM4, RASSF1A and OSMR can be from any tissue sample, body fluid, body fluid precipitate or lavage specimen. Preferably, the test sample is obtained from a human subject. Test samples for diagnostic, prognostic, or personalised medicinal uses can be obtained from surgical samples, such as biopsies or fine needle aspirates, from paraffin embedded tissues, from frozen tumor tissue samples, from fresh tumor tissue samples, from a fresh or frozen body fluid, for example. Non-limiting examples include whole blood, bone marrow, cerebral spinal fluid, peritoneal fluid, pleural fluid, lymph fluid, serum, plasma, urine, chyle, stool, ejaculate, sputum, nipple aspirate, saliva, swabs specimen, wash or lavage fluid and/or brush specimens.

Preferably the test sample is taken from a human subject and contains (transitional) bladder cells or nucleic acid from (transitional) bladder cells. Alternatively, the test sample contains squamous carcinoma bladder cells or nucleic acid from squamous cell carcinomas. Preferably, it is obtained from a bladder tissue. More preferably, the test sample is derived from urine. The sample may contain nucleic acid from transitional bladder cells or squamous carcinoma bladder cells. The test sample can be derived from liquid urine, a precipitate thereof, or a precipitate in the urine. The tissues and body fluids can be collected using any of the methods well known in the art. The "nucleic acid" in the methods according to the invention is preferably deoxyribonucleic acid (DNA), in particular genomic DNA.

In embodiments where urine samples are employed, they may be processed according to any suitable procedure. In certain embodiments, the methods of the invention additionally comprise stabilising the urine sample. It is shown herein that stabilising the urine sample, by adding a suitable stabilizing buffer to the urine, may avoid the need for centrifugation of the urine sample shortly after obtaining the sample. Typically centrifugation occurs within 4 hours of obtaining the urine sample in order to maintain the integrity of the DNA (in particular in the sediment fraction). The samples can be maintained at room temperature for up to 48 or 72 hours or more following addition of a stabilizing buffer, without the requirement for centrifugation. This advantageously permits home collection of urine samples and also removes the necessity for centrifugation equipment at each collection site. Thus, the methods of the invention may incorporate methods for conveniently storing urine samples for a period of up to 72 (or 48) hours or more at room temperature, such as at least 4, 12, 24, 36 or 48 hours up to 72 hours or more, comprising adding a stabilising buffer to the urine sample, with the proviso that the urine sample is not centrifuged or otherwise fractionated prior to or during the storage period and storing the urine for this period. The urine sample can be stored according to these methods for longer periods than 72 hours provided that the integrity of the DNA in the sample is maintained (thus allowing the methods of the invention to be carried out). Following the storage period, the sample may then be centrifuged as part of the methods of the invention. The thus centrifuged sample may be stored under appropriate conditions, as discussed herein, such as at 4° C. or at −20° C. Suitable stabilizing buffers for use in these methods are described herein. Any suitable stabilizing buffer may be employed.

Whilst stabilization may be achieved via any suitable means, in preferred embodiments, stabilisation occurs through addition of a stabilising buffer. The stabilising buffer incorporates suitable components to maintain DNA integrity in the urine sample and/or to maintain the quality of the urine sample as a whole. Thus, the methods and kits of the invention may employ a stabilising buffer solution for storing urine samples comprising EDTA and/or DMSO and/or an antibacterial and/or STABILUR™ tablet. In specific embodiments, the stabilising buffer comprises EDTA, an antibacterial and optionally a STABILUR™ tablet. This solution may be used for storing a urine sample at a temperature of around 4° C. or at other temperatures, such as room temperature. In a related aspect, the methods and kits of the invention may employ a stabilising buffer for storing urine samples comprising EDTA, DMSO and an antibacterial. The solution may be used for storing a urine sample under freezing conditions or at other temperatures, such as room temperature. These buffer solutions are useful for storing whole urine samples. They are useful for storing the cell-free DNA component from a urine sample and/or the pellet fraction produced typically by (low speed) centrifugation. Typically, the stabilising buffer is added to the urine sample shortly after collection of the sample. This is then stored, according to the methods described herein, for up to 72 hours or more prior to centrifugation. The sample may then be centrifuged prior to further processing according to the methods of the invention. Following centrifugation, the samples—such as the sediment and/or or pellet portion of the sample—may then be stored for longer periods of time, for example at a temperature such as −20° C. for up to 6 months or longer.

The stabilising buffer for use in methods of the invention may comprise, consist essentially of or consist of at least one component selected from EDTA, an antibacterial, DMSO and STABILUR™ tablets. STABILUR tablets are available from Cargille Labs and contain appropriate mixtures of buffering and osmolarity adjustment ingredients. Suitable equivalents to this product may be utilised as appropriate, such as preservative tubes available from CellSave (Cell-Save Preservative Tubes).

The term "antibacterial" is intended to cover any compound, molecule or otherwise which has an inhibitory effect on the growth or viability of one or more bacteria. Both biological and non-biological molecules are intended to fall within the definition. In certain embodiments, the antibacterial comprises, consists essentially of or consists of an antibiotic. Many antibiotics are well known in the art and commercially available. Mixtures of antibiotics may be utilised as appropriate, such as the Antibiotic-Antimycotic A5955-100 ml antibiotic mix available from Sigma-Aldrich.

Suitable anti-bacterials may include cytokines such as interferons and interleukins and derivatives and mimetics thereof, for example as described in WO 2006/123164 (which reference is incorporated herein in its entirety) and "small molecules". A small molecule is defined as a molecular entity with a molecular weight of less than 1500 daltons, preferably less than 1000 daltons. The small molecule may for example be an organic, inorganic or organometallic molecule, which may also be in the form or a suitable salt, such as a water-soluble salt; and may also be a complex, chelate and/or a similar molecular entity, as long as its (overall) molecular weight is within the range indicated above.

In specific embodiments the EDTA is present at a final concentration of around 10 mM and/or the DMSO is present at around 10% of the final stabilising buffer volume.

Samples (to which a stabilising buffer has been added) may be stored at any suitable temperature, including room temperature. For example, the storage temperature may be anywhere between approximately −50° C. and approximately 37° C., preferably approximately −10° C. to −30° C., such as approximately −20° C. or approximately 1° C. to 10° C., such as approximately 4° C. By "freezing" is meant a temperature at or below 0° C., preferably approximately −20° C.

Present methods may also include the step of obtaining the test sample. The tissue sample or liquid sample comprising the nucleic acid may be lysed or need to be concentrated to create a mixture of biological compounds comprising nucleic acids and other components. Alternatively, the nucleic acid may need to be cleared of proteins or other contaminants, e.g. by treatment with proteinase K. Procedures for lysing or concentrating biological samples are known by the person skilled in the art and can be chemical, enzymatic or physical in nature. A combination of these procedures may be applicable as well. For instance, lysis may be performed using ultrasound, high pressure, shear forces, alkali, detergents or chaotropic saline solutions, or proteases or lipases. For the lysis procedure to obtain nucleic acids, or concentrating nucleic acid from samples, reference may be made to Sambrook, J., et al., Molecular cloning: A Laboratory Manual, (2001) 3rd edition, Cold Spring Harbor Laboratory Press, Cold Spring Harbor, N.Y. Ausubel, F. M., et al., Current Protocols in Molecular Biology (1987), J. Wiley and Sons, New York. In certain embodiments, nucleic acids are extracted from the test sample using a commercially available purification kit, such as the PUREGENE® DNA purification kit. In specific embodiments, the sample may be centrifuged and nucleic acid purified from the sediment or pellet fraction, in particular using such a purification kit. Suitable purification kits are commercially available and would be well known to one skilled in the art.

The test sample is generally obtained from a (human) subject suspected of being tumorigenic. Alternatively the test sample is obtained from a subject undergoing routine examination and not necessarily being suspected of having a disease. Thus patients at risk can be identified before the disease has a chance to manifest itself in terms of symptoms identifiable in the patient. Alternatively the sample is obtained from a subject undergoing treatment, or from patients being checked for recurrence of disease.

"Detecting" a disease or predisposition to disease is defined herein to include detecting by way of routine examination, screening for a disease or pre-stadia of a disease, monitoring and/or staging the state and/or progression of the disease, checking for recurrence of disease following treatment and monitoring the success of a particular treatment. The detection can also have prognostic value, and the prognostic value of the tests can be used as a marker of potential susceptibility to cancer. The detection may also link to a cancer stage or grade.

The "Stage" refers to how far a cancer has progressed anatomically, while the "grade" refers to cell appearance (differentiation) and DNA make up.

"Cancer" refers to the presence of cells possessing characteristics typical of cancer-causing cells, such as uncontrolled proliferation, immortality, metastatic potential, rapid growth and proliferation rate, and certain characteristic morphological features. The particular cancer type relevant to the invention is bladder cancer.

"Bladder cancer" is defined to include transitional cell carcinoma or squamous cell carcinomas. The cancer may concern superficial bladder cancer, invasive bladder cancer, or metastatic bladder cancer. Superficial cancer is only in cells in the lining of the bladder and has high grade of recurrence. Superficial tumor may grow through the lining into the muscular wall of the bladder and become invasive cancer. Invasive cancer can extend through the bladder wall and can grow into a nearby organ such as the uterus or vagina (in women) or the prostate gland (in men). It also may invade the wall of the abdomen. The cancer becomes metastatic when it spreads outside the bladder into nearby lymph nodes and other organs, such as the lungs, liver, or bones.

"Epigenetic change" is defined to include herein alterations resulting in diminished gene expression potential, mediated by mechanisms other than alterations in the primary nucleotide sequence of a gene. Three related mechanisms that cause epigenetic alteration in gene expression are DNA methylation, histone code changes and RNA interference. The epigenetic change is generally epigenetic silencing in this invention. Epigenetic silencing is preferably caused by DNA methylation.

The epigenetic change in the genes of present invention is generally epigenetic silencing caused by DNA methylation. Thus, the invention provides for a method of detecting a predisposition to, or the incidence of, bladder cancer in a sample comprising detecting epigenetic silencing in at least one gene selected from NID2, TJP2, TWIST1, TNFRSF25, BMP7, RUNX3, CCNA1, APC, LOXL1, TUBB4, NTRK2, ARFGAP3, PDLIM4, RASSF1A and OSMR, wherein epigenetic silencing of the at least one gene is detected by determination of the methylation status of the gene and wherein methylation of the gene is indicative of a predisposition to, or the incidence of, bladder cancer.

The term "methylation state" or "methylation status" refers to the presence or absence of a methylated cytosine residue in one or more CpG dinucleotides within a nucleic acid. In many genes, the CpG islands begin just upstream of a promoter and extend downstream into the transcribed region. Methylation of a CpG island at a promoter usually prevents expression of the gene. The islands can also surround the 5' region of the coding region of the gene as well as the 3' region of the coding region. Thus, CpG islands can be found in multiple regions of a nucleic acid sequence including upstream of coding sequences in a regulatory region including a promoter region, in the coding regions (e.g., exons), downstream of coding regions in, for example, enhancer regions, and in introns. All of these regions can be assessed to determine their methylation status, as appropriate In a preferred embodiment, the methylation status of the promoter region of the at least one gene selected from NID2, TJP2, TWIST1, TNFRSF25, BMP7, RUNX3, CCNA1, APC, LOXL1, TUBB4, NTRK2, ARFGAP3, PDLIM4, RASSF1A and OSMR is determined. A "promoter" is a region extending typically between approximately 1 Kb, 500 bp or 150 to 300 bp upstream from the transcription start site. Preferably, the CpG island which surrounds or is positioned around the transcription start site of the at least one gene selected from NID2, TJP2, TWIST1, TNFRSF25, BMP7, RUNX3, CCNA1, APC, LOXL1, TUBB4, NTRK2, ARFGAP3, PDLIM4, RASSF1A and OSMR, is analysed to determine its methylation status. Alternatively, the methylation status of the exon and/or intron regions of the at least one gene selected from NID2, TJP2, TWIST1, TNFRSF25, BMP7, RUNX3, CCNA1, APC, LOXL1, TUBB4, NTRK2, ARFGAP3, PDLIM4, RASSF1A and OSMR, may be determined as appropriate.

Various techniques for assessing methylation status are known in the art and can be used in conjunction with the present invention: sequencing, methylation-specific PCR (MS-PCR), melting curve methylation-specific PCR (McMS-PCR), MLPA with or without bisulphite treatment, QAMA (Zeschnigk et al, 2004), MSRE-PCR (Melnikov et al, 2005), MethyLight (Eads et al., 2000), ConLight-MSP (Rand et al., 2002), bisulphite conversion-specific methylation-specific PCR (BS-MSP) (Sasaki et al., 2003), COBRA (which relies upon use of restriction enzymes to reveal methylation dependent sequence differences in PCR products of sodium bisulphite—treated DNA), methylation-sensitive single-nucleotide primer extension conformation (MS-SNuPE), methylation-sensitive single-strand conformation analysis (MS-SSCA), Melting curve combined bisulphite restriction analysis (McCOBRA) (Akey et al., 2002), PyroMethA, HeavyMethyl (Cottrell et al. 2004), MALDI-TOF, MassARRAY, Quantitative analysis of methylated alleles (QAMA), enzymatic regional methylation assay (ERMA), QBSUPT, MethylQuant, Quantitative PCR sequencing and oligonucleotide-based microarray systems, Pyrosequencing, Meth-DOP-PCR. A review of some useful techniques for DNA methylation analysis is provided in Nucleic acids research, 1998, Vol. 26, No. 10, 2255-2264, Nature Reviews, 2003, Vol. 3, 253-266; Oral Oncology, 2006, Vol. 42, 5-13, which references are incorporated herein in their entirety.

Techniques for assessing methylation status are based on distinct approaches. Some include use of endonucleases. Such endonucleases may either preferentially cleave methylated recognition sites relative to non-methylated recognition sites or preferentially cleave non-methylated relative to methylated recognition sites. Some examples of the former are Acc III, Ban I, BstN I, Msp I, and Xma I. Examples of the latter are Acc II, Ava I, BssH II, BstU I, Hpa II, and Not I. Differences in cleavage pattern are indicative for the presence or absence of a methylated CpG dinucleotide. Cleavage patterns can be detected directly, or after a further reaction which creates products which are easily distinguishable. Means which detect altered size and/or charge can be used to detect modified products, including but not limited to electrophoresis, chromatography, and mass spectrometry.

Alternatively, the identification of methylated CpG dinucleotides may utilize the ability of the methyl binding domain (MBD) of the MeCP2 protein to selectively bind to methylated DNA sequences (Cross et al, 1994; Shiraishi et al, 1999). The MBD may also be obtained from MBP, MBP2, MBP4, poly-MBD (Jorgensen et al., 2006) or from reagents such as antibodies binding to methylated nucleic acid. The MBD may be immobilized to a solid matrix and used for preparative column chromatography to isolate highly methylated DNA sequences. Variant forms such as expressed His-tagged methyl-CpG binding domain may be used to selectively bind to methylated DNA sequences. Eventually, restriction endonuclease digested genomic DNA is contacted with expressed His-tagged methyl-CpG binding domain. Other methods are well known in the art and include amongst others methylated-CpG island recovery assay (MIRA). Another method, MB-PCR, uses a recombinant, bivalent methyl-CpG-binding polypeptide immobilized on the walls of a PCR vessel to capture methylated DNA and the subsequent detection of bound methylated DNA by PCR.

Further approaches for detecting methylated CpG dinucleotide motifs use chemical reagents that selectively modify either the methylated or non-methylated form of CpG dinucleotide motifs. Suitable chemical reagents include hydrazine and bisulphite ions. The methods of the invention preferably use bisulphite ions. The bisulphite conversion relies on treatment of DNA samples with sodium bisulphite which converts unmethylated cytosine to uracil, while methylated cytosines are maintained (Furuichi et al., 1970). This conversion finally results in a change in the sequence of the original DNA. It is general knowledge that the resulting uracil has the base pairing behaviour of thymidine which differs from cytosine base pairing behaviour. This makes the discrimination between methylated and non-methylated cytosines possible. Useful conventional techniques of molecular biology and nucleic acid chemistry for assessing sequence differences are well known in the art and explained in the literature. See, for example, Sambrook, J., et al., Molecular cloning: A laboratory Manual, (2001) $3^{rd}$ edition, Cold Spring Harbor, N.Y.; Gait, M. J. (ed.), Oligonucleotide Synthesis, A Practical Approach, IRL Press (1984); Hames B. D., and Higgins, S. J. (eds.), Nucleic Acid Hybridization, A Practical Approach, IRL Press (1985); and the series, Methods in Enzymology, Academic Press, Inc.

Some techniques use primers for assessing the methylation status at CpG dinucleotides. Two approaches to primer design are possible. Firstly, primers may be designed that themselves do not cover any potential sites of DNA methylation. Sequence variations at sites of differential methylation are located between the two primers and visualisation of the sequence variation requires further assay steps. Such primers are used in bisulphite genomic sequencing, COBRA, Ms-SnuPE and several other techniques. Secondly, primers may be designed that hybridize specifically with either the methylated or unmethylated version of the initial treated sequence. After hybridization, an amplification reaction can be performed and amplification products assayed using any detection system known in the art. The presence of an amplification product indicates that a sample hybridized to the primer. The specificity of the primer indicates whether the DNA had been modified or not, which in turn indicates whether the DNA had been methylated or not. If there is a sufficient region of complementarity, e.g., 12, 15, 18, or 20 nucleotides, to the target, then the primer may also contain additional nucleotide residues that do not interfere with hybridization but may be useful for other manipulations. Examples of such other residues may be sites for restriction endonuclease cleavage, for ligand binding or for factor binding or linkers or repeats. The oligonucleotide primers may or may not be such that they are specific for modified methylated residues.

A further way to distinguish between modified and unmodified nucleic acid is to use oligonucleotide probes. Such probes may hybridize directly to modified nucleic acid or to further products of modified nucleic acid, such as products obtained by amplification. Probe-based assays exploit the oligonucleotide hybridisation to specific sequences and subsequent detection of the hybrid. There may also be further purification steps before the amplification product is detected e.g. a precipitation step. Oligonucleotide probes may be labelled using any detection system known in the art. These include but are not limited to fluorescent moieties, radioisotope labelled moieties, bioluminescent moieties, luminescent moieties, chemiluminescent moieties, enzymes, substrates, receptors, or ligands.

In a most preferred embodiment, the methylation status of the at least one gene selected from NID2, TJP2, TWIST1, TNFRSF25, BMP7, RUNX3, CCNA1, APC, LOXL1, TUBB4, NTRK2, ARFGAP3, PDLIM4, RASSF1A and OSMR, (or portion thereof, especially the CpG islands, as discussed herein) is determined using methylation specific PCR (MSP), or an equivalent amplification technique. In the MSP approach, DNA may be amplified using primer pairs designed to distinguish methylated from unmethylated DNA by taking advantage of sequence differences as a result of sodium-bisulphite treatment (Herman et al., 1996; and WO 97/46705). For example, bisulphite ions modify non-methylated cytosine bases, changing them to uracil bases. Uracil bases hybridize to adenine bases under hybridization conditions. Thus an oligonucleotide primer which comprises adenine bases in place of guanine bases would hybridize to the bisulphite-modified DNA, whereas an oligonucleotide primer containing the guanine bases would hybridize to the non-modified (methylated) cytosine residues in the DNA. Amplification using a DNA polymerase and a second primer yield amplification products which can be readily observed, which in turn indicates whether the DNA had been methylated or not. Whereas PCR is a preferred amplification method, variants on this basic technique such as nested PCR and multiplex PCR are also included within the scope of the invention.

Bisulphite sequencing offers another preferred alternative to determine the methylation status of at least one gene selected from NID2, TJP2, TWIST1, TNFRSF25, BMP7, RUNX3, CCNA1, APC, LOXL1, TUBB4, NTRK2, ARFGAP3, PDLIM4, RASSF1A and OSMR. Primers may be designed for use in sequencing through the important CpG islands of the concerned gene. Thus, primers may be designed in both the sense and antisense orientation to direct sequencing across the region of interest of the selected gene.

As mentioned earlier, a preferred embodiment for assessing the methylation status of the relevant gene requires amplification to yield amplification products. The presence of amplification products may be assessed directly using methods well known in the art. They simply may be visualized on a suitable gel, such as an agarose or polyacrylamide gel. Detection may involve the binding of specific dyes, such as ethidium bromide, which intercalate into double-stranded DNA and visualisation of the DNA bands under a UV illuminator for example. Another means for detecting amplification products comprises hybridization with oligonucleotide probes. Alternatively, fluorescence or energy transfer can be measured to determine the presence of the methylated DNA.

A specific example of the MSP technique is designated real-time quantitative MSP (QMSP), and permits reliable quantification of methylated DNA in real time or at end point. Real-time methods are generally based on the continuous optical monitoring of an amplification procedure and utilise fluorescently labelled reagents whose incorporation in a product can be quantified and whose quantification is indicative of copy number of that sequence in the template. One such reagent is a fluorescent dye, called SYBR Green I that preferentially binds double-stranded DNA and whose fluorescence is greatly enhanced by binding of double-stranded DNA. Alternatively, labeled primers and/or labeled probes can be used for quantification. They represent a specific application of the well known and commercially available real-time amplification techniques such as TAQMAN®, MOLECULAR BEACONS®, AMPLIFLUOR® and SCORPION® DzyNA®, Plexor™ etc.

Accordingly, in a further embodiment, the methylation status of at least one gene selected from NID2, TJP2, TWIST1, TNFRSF25, BMP7, RUNX3, CCNA1, APC, LOXL1, TUBB4, NTRK2, ARFGAP3, PDLIM4, RASSF1A and OSMR, is determined by methylation specific PCR, preferably real-time or end point methylation specific PCR. In specific embodiments, the real-time or end point methylation specific PCR comprises use of TAQMAN probes and/or MOLECULAR BEACONS and/or AMPLIFLUOR primers and/or FRET probes and/or SCORPION primers and/or oligonucleotide blockers and/or DzyNA primers.

In the real-time PCR system, it is possible to monitor the PCR reaction during the exponential phase where the first significant increase in the amount of PCR product correlates to the initial amount of target template. TaqMan technology uses linear, hydrolytic oligonucleotide probes that contain a fluorescent dye and a quenching dye. When irradiated, the excited fluorescent dye transfers energy to the nearby quenching dye molecule rather than fluoresencing (FRET principle). TaqMan probes anneal to an internal region of the PCR product and are cleaved by the exonuclease activity of the polymerase when it replicates a template. This ends the activity of the quencher, and the reporter dye starts to emit fluorescence which increases in each cycle proportional to the rate of probe cleavage.

Molecular beacons also contain fluorescent and quenching dyes, but they are designed to adopt a hairpin structure while free in solution to bring both dyes in close proximity for FRET to occur. When the beacon hybridises to the target during the annealing step, both dyes (donor and acceptor/quencher) are separated and an increase in fluorescence correlates with the amount of PCR product available. The experiments described herein show that molecular beacons are particularly useful for monitoring the amplification/PCR reaction during the exponential phase. Thus, molecular beacons may advantageously be employed in certain embodiments of the invention.

With scorpion probes, sequence-specific priming and PCR product detection is achieved using a single oligonucleotide. The scorpion probe maintains a stem-loop configuration in the unhybridized state and FRET occurs. The 3' portion of the stem also contains a sequence that is complementary to the extension product of the primer. This sequence is linked to the 5' end of a specific primer via a non-amplifiable monomer. After extension of the scorpion primer, the specific probe sequence is able to bind to its complement within the extended amplicon, thus opening up the hairpin loop and providing a fluorescence signal.

In similar fashion to Scorpions, The Amplifluor technique relies upon incorporation of a Molecular Beacon type probe into a primer. Again, the hairpin structure of the probe forms part of an amplification primer itself. However, in contrast to Scorpions type primers, there is no block at the 5' end of the probe in order to prevent it being amplified and forming part of an amplification product. Accordingly, the primer binds to a template strand and directs synthesis of the complementary strand. The primer therefore becomes part of the amplification product in the first round of amplification. When the complimentary strand is synthesised amplification occurs through the hairpin structure. This separates the fluorophore and quencher molecules, thus leading to generation of fluorescence as amplification proceeds.

In a variant Amplifluor format, the sequence-specific primer carries a "Z" sequence addition at its 5' end and yields an initial amplification product that contains the complement of the "Z" sequence. A second primer with stem-loop configuration is designed to contain the "Z" sequence and anneals to the template containing the complement of "Z". During the polymerization reaction the reporter and quencher molecules are incorporated into the product. This product serves as a template for further amplification. As the hairpin conformation of the template becomes unfolded during polymerization, a fluorescence signal is observed.

In Heavymethyl, the priming is methylation specific, but non-extendable oligonucleotide blockers provide this specificity instead of the primers themselves. The blockers bind to bisulphite-treated DNA in a methylation-specific manner, and their binding sites overlap the primer binding sites. When the blocker is bound, the primer cannot bind and therefore the amplicon is not generated. Heavymethyl can be used in combination with real-time or end point detection.

The Plexor™ qPCR and qRT-PCR Systems take advantage of the specific interaction between two modified nucleotides to achieve quantitative PCR analysis. One of the PCR primers contains a fluorescent label adjacent to an iso-dC residue at the 5' terminus. The second PCR primer is unlabeled. The reaction mix includes deoxynucleotides and iso-dGTP modified with the quencher dabcyl. Dabcyl-iso-dGTP is preferentially incorporated at the position complementary to the iso-dC residue. The incorporation of the dabcyl-iso-dGTP at this position results in quenching of the fluorescent dye on the complementary strand and a reduction in fluorescence, which allows quantitation during amplification. For these multiplex reactions, a primer pair with a different fluorophore is used for each target sequence.

Real-Time PCR detects the accumulation of amplicon during the reaction. Real-time methods do not need to be utilised, however. Many applications do not require quantification and Real-Time PCR is used only as a tool to obtain convenient results presentation and storage, and at the same time to avoid post-PCR handling. Thus, analyses can be performed only to confirm whether the target DNA is present in the sample or not. Such end-point verification is carried out after the amplification reaction has finished. This knowledge can be used in a medical diagnostic laboratory to detect a predisposition to, or the incidence of, cancer in a patient. End-point PCR fluorescence detection techniques can use the same approaches as widely used for Real Time PCR. For example, <<Gene>> detector allows the measurement of fluorescence directly in PCR tubes. Accordingly, in a further preferred embodiment, the methylation status of at least one gene selected from NID2, TJP2, TWIST1, TNFRSF25, BMP7, RUNX3, CCNA1, APC, LOXL1, TUBB4, NTRK2, ARFGAP3, PDLIM4, RASSF1A and OSMR, is determined by methylation specific PCR amplification and, preferably the methylation specific PCR is monitored at the end-point of the amplification.

In one particular embodiment, primers useful in MSP carried out on the gene selected from NID2, TJP2, TWIST1, TNFRSF25, BMP7, RUNX3, CCNA1, APC, LOXL1, TUBB4, NTRK2, ARFGAP3, PDLIM4, RASSF1A and OSMR are provided. Primers of the invention preferably are designed to bind to fully methylated genomic sequences in the regions under investigation. These primers may comprise, consist essentially of or consist of the following sequences:

```
S = sense primer (5' - 3')
AS = antisense primer (5' - 3')
MB = molecular beacon (modification beacons:
5' FAM, 3' DABCYL)

RASSF1A_S (SEQ ID NO. 1):
GCGTTGAAGTCGGGGTTC

RASSF1A_AS (SEQ ID NO. 2):
CCCGTACTTCGCT2AACTTTAAACG

RASSF1A_MB (SEQ ID NO. 3):
CGTCTGCGTGGTTTCGTTCGGTTCGCGTTTGTTAGGCAGACG

APC(2)_S (SEQ ID NO. 4):
TAT TGC GGA GTG CGG GTC

APC(2)_AS (SEQ ID NO. 5):
TCG ACG AAC TCC CGA CGA

APC(2)_MB (SEQ ID NO. 6):
CGACATGCGTGTAATTCGTTGGATGCGGATTAGGGCGGCATGTCG

CCNA1_gron_S (SEQ ID NO. 7):
GTTATGGCGATGCGGTTTC

CCNA1_gron_AS (SEQ ID NO. 8):
CCAACCTAAAAAACGACCGA

CCNA1_gron_MB (SEQ ID NO. 9):
CGACATGCACGACGCCCCCGAACCTAACGCATGTCG

TNERSF25_1_S (SEQ ID NO. 10):
GTCGTCGAGAAGGGTTCGTTT

TNERSF25_1_AS (SEQ ID NO. 11):
GCGTATTCTACTTAACCTATCCGC

TNERSF25_1_MB (SEQ ID NO. 12):
CGACATGCACGACCCCGCCTCCCCCCGCCGCATGTCG

TUBB4_2_S (SEQ ID NO. 13):
TAAATTAGATCGTCGTTTCGGAG

TUBB4_2_AS (SEQ ID NO. 14):
TACCTCAATTTCTCGATCCGC

TUBB4_2_MB (SEQ ID NO. 15):
CGACATGCTGGGAGGGTTCGCGGTTATTGTAAGGAGCATGTCG

NTRK2_1_M_S (SEQ ID NO. 16):
GTTAGAGCGCGTTTTTAGCGT

NTRK2_1_M_AS (SEQ ID NO. 17):
CCGCAATACCTAACACTTCCG

NTRK2_1_MB (SEQ ID NO. 18)
CGACATGCCCGACACGCTCCGAAACACCAGCATGTCG

OSMR_1_S (SEQ ID NO. 19):
GTGTTAAGAGTGCGTAGTAAGACG

OSMR_1_AS (SEQ ID NO. 20):
GAAACGAACGTACAAAAACGA

OSMR_1_MB (SEQ ID NO. 21):
CGACATGCCGAAACTATAAATCAACTACGAAACAAACGCGCATGTCG

TWIST1_3_S (SEQ ID NO. 22)
GTTAGGGTTCGGGGGCGTTGTT

TWIST1_3_AS (SEQ ID NO. 23):
CCGTCGCCTTCCTCCGACGAA

TWIST1_3_MB (SEQ ID NO. 24):
CGACATGCCGGCGGGGAAGGAAATCGTTTCGCATGTCG

LOXL1_29309_S (SEQ ID NO. 25):
TAGAGTACGTGTCGGTCGGAT

LOXL1_29309_AS (SEQ ID NO. 26):
ACAAAAACAAAAACGACGCCT

MB_LOXL1_29309b (SEQ ID NO. 27)
CGACATGCCGGGTGTTGTTGGTCGGCGCGCATGTCG

TJP2_25301_S (SEQ ID NO. 28):
GAGATCGCGGGTTTTATTTC

TJP2_25301_AS (SEQ ID NO. 29):
CCAACTTCCTACGACGCAT

TJP2_25301_MB (SEQ ID NO. 30):
CGACATGCCTCCCAACCGCGCGACACAAGCATGTCG

Runx3_3_M_S (SEQ ID NO. 31):
CGTAGGGTTGTATTTGAGCGA

Runx3_3_M_AS (SEQ ID NO. 32):
TAACTTTTAACGAAATTACCCCG

RUNX3_3_MB2 (SEQ ID NO. 33):
CGACATGCCGGGTTAGGGGGGCGTAAAATTTTATTCGTTGCATGTCG

PDLIM4_4_M_S (SEQ ID NO. 34):
GGCGTTTAGGTTAATTTTTCGT

PDLIM4_4_M_AS (SEQ ID NO. 35):
CGATCCCATATCTAAAACCGA

PDLIM4_4_MB (SEQ ID NO. 36):
CGACATGCCTCGCGATCCGCCCGAAACGCATGTCG

BMP7_17911_S (SEQ ID NO. 37):
AGCGTAGAGATAGGTTGGTAACG

BMP7_17911_AS (SEQ ID NO. 38):
AAAACGATAACCCTTAAACCGA

MB_BMP7_17911 (SEQ ID NO. 39):
CGACATGCGCGGAGGGGTTAGCGTGGTTGCATGTCG

NID2_9091_S (SEQ ID NO. 40):
GCGGTTTTTAAGGAGTTTTATTTTC

NID2_9091_AS (SEQ ID NO. 41):
CTACGAAATTCCCTTTACGCT

MB_NID2_9091 (SEQ ID NO. 42):
CGACATGGGTTCGTAAGGTTTGGGGTAGCGGCCATGTCG

ARFGAP3_25342_S (SEQ ID NO. 43):
GCGTTAAGGTACGGGTTTTC

ARFGAP3_25342_A (SEQ ID NO. 44):
GCCATTTCGCCTAACGAAC

ARFGAP3_25342_MB (SEQ ID NO. 45):
CGACATGCACGCGCCCTCCTTCGACACGCATGTCG
```

Further characteristics of these primers are summarized in the experimental part. It is noted that variants of these sequences may be utilised in the present invention. In particular, additional flanking sequences may be added, for example to improve binding specificity, as required. Variant sequences preferably have at least 90%, at least 91%, at least 92%, at least 93%, at least 94%, at least 95%, at least 96%, at least 97%, at least 98%, or at least 99% nucleotide sequence identity with the nucleotide sequences of the primers and/or probes set forth herein. The primers and probes may incorporate synthetic nucleotide analogues as appropriate or may be DNA, RNA or PNA based for example, or mixtures thereof. Similarly alternative fluorescent donor and acceptor moieties/FRET pairs may be utilised as appropriate. In addition to being labelled with the fluorescent donor and acceptor moieties, the primers and probes may include modified oligonucleotides and other appending groups and labels provided that the functionality as a primer and/or probe in the methods of the invention is not compromised.

In real-time embodiments, quantitation may be on an absolute basis, or may be relative to a constitutively methylated DNA standard, or may be relative to an unmethylated DNA standard. Methylation status may be determined by using the ratio between the signal of the marker under investigation and the signal of a reference gene where methylation status is known (such as β-actin for example), or by using the ratio between the methylated marker and the sum of the methylated and the non-methylated marker. Alternatively, absolute copy number of the methylated marker gene can be determined.

Suitable controls may need to be incorporated in order to ensure the method chosen is working correctly and reliably. Suitable controls may include assessing the methylation status of a gene known to be methylated. This experiment acts as a positive control to ensure that false negative results are not obtained. The gene may be one which is known to be methylated in the sample under investigation or it may have been artificially methylated, for example by using a suitable methyltransferase enzyme, such as SssI methyltransferase. In one embodiment, the gene selected from NID2, TJP2, TWIST1, TNFRSF25, BMP7, RUNX3, CCNA1, APC, LOXL1, TUBB4, NTRK2, ARFGAP3, PDLIM4, RASSF1A and OSMR, may be assessed in normal cells, following treatment with SssI methyltransferase, as a positive control.

Additionally or alternatively, suitable negative controls may be employed with the methods of the invention. Here, suitable controls may include assessing the methylation status of a gene known to be unmethylated or a gene that has been artificially demethylated. This experiment acts as a negative control to ensure that false positive results are not obtained. In one embodiment, the gene selected from NID2, TJP2, TWIST1, TNFRSF25, BMP7, RUNX3, CCNA1, APC, LOXL1, TUBB4, NTRK2, ARFGAP3, PDLIM4, RASSF1A and OSMR may be assessed in normal cells as a negative control, since it has been shown for the first time herein that the gene selected from NID2, TJP2, TWIST1, TNFRSF25, BMP7, RUNX3, CCNA1, APC, LOXL1, TUBB4, NTRK2, ARFGAP3, PDLIM4, RASSF1A and OSMR is unmethylated in normal tissues.

Whilst PCR is the preferred nucleic acid amplification technique, other amplification techniques may also be utilised to detect the methylation status of the concerned gene. Such amplification techniques are well known in the art, and include methods such as NASBA (Compton, 1991), 3SR (Fahy et al., 1991) and Transcription Mediated Amplification (TMA). Other suitable amplification methods include the ligase chain reaction (LCR) (Barringer et al, 1990), selective amplification of target polynucleotide sequences (U.S. Pat. No. 6,410,276), consensus sequence primed polymerase chain reaction (U.S. Pat. No. 4,437,975), arbitrarily primed polymerase chain reaction (WO 90/06995), invader technology, strand displacement technology, and nick displacement amplification (WO 2004/067726). This list is not intended to be exhaustive; any nucleic acid amplification technique may be used provided the appropriate nucleic acid product is specifically amplified. Thus, these amplification techniques may be tied in to MSP and/or bisulphite sequencing techniques for example.

The application of the methods of present invention on exceeding small amounts of abnormally-methylated DNA, that are released into collected fluids such as e.g. serum, urine, wash specimen etc. . . . , may require the generation and amplification of a DNA library before testing for methylation of any specific gene. Suitable methods on whole genome amplification and libraries generation for such amplification (e.g. Methylplex and Enzyplex technology, Rubicon Genomics) are described in US2003/0143599, WO2004/081225 and WO2004/081183. In addition, WO2005/090507 regards library generation/amplification methods that require either bisulphite conversion or non-bisulphite based application. Bisulphite treatment may occur before or after library construction and may require the use of adaptors resistant to bisulphite conversion. Meth-DOP-PCR (Di Vinci et al, 2006), a modified degenerate oligonucleotide-primed PCR amplification (DOP-PCR) that is combined with MSP, provides another suitable method for specific detection of methylation in small amount of DNA. Improved management of patient care may require these existing methods and techniques to supplement the methods of the invention.

Since epigenetic silencing of a gene manifests itself most frequently in diminished expression in tumor cells, the invention provides for a method of detecting cancer or predisposition to cancer, in particular bladder cancer comprising detecting epigenetic silencing of at least one gene selected from NID2, TJP2, TWIST1, TNFRSF25, BMP7, RUNX3, CCNA1, APC, LOXL1, TUBB4, NTRK2, ARFGAP3, PDLIM4, RASSF1A and OSMR, wherein epigenetic silencing of the gene at least one gene is determined by measurement of expression levels of the gene and wherein reduced expression of the gene is indicative for cancer or predisposition to cancer.

Total loss of protein expression of the gene selected from NID2, TJP2, TWIST1, TNFRSF25, BMP7, RUNX3, CCNA1, APC, LOXL1, TUBB4, NTRK2, ARFGAP3, PDLIM4, RASSF1A and OSMR gene may be observed in the sample in order to conclude a diagnosis of cancer or predisposition to cancer, in particular bladder cancer, or to make a decision on the best course of treatment in accordance with the other methods of the invention. However, partial loss of the gene expression of the gene selected from NID2, TJP2, TWIST1, TNFRSF25, BMP7, RUNX3, CCNA1, APC, LOXL1, TUBB4, NTRK2, ARFGAP3, PDLIM4, RASSF1A and OSMR may also be relevant, due to methylation of the relevant gene.

The decreased level of expression of gene selected from NID2, TJP2, TWIST1, TNFRSF25, BMP7, RUNX3, CCNA1, APC, LOXL1, TUBB4, NTRK2, ARFGAP3, PDLIM4, RASSF1A and OSMR may, as necessary, be measured in order to determine if it is statistically significant in the sample. This helps to provide a reliable test for the methods of the invention. Any method for determining whether the expression level of the gene selected from NID2, TJP2, TWIST1, TNFRSF25, BMP7, RUNX3, CCNA1, APC, LOXL1, TUBB4, NTRK2, ARFGAP3, PDLIM4, RASSF1A and OSMR is significantly reduced may be utilised.

Such methods are well known in the art and routinely employed. For example, statistical analyses may be performed using an analysis of variance test. Typical P values for use in such a method would be P values of <0.05 or 0.01 or 0.001 when determining whether the relative expression or activity is statistically significant. A change in expression may be deemed significant if there is at least a 10% decrease for example. The test may be made more selective by making the change at least 15%, 20%, 25%, 30%, 35%, 40% or 50%, for example, in order to be considered statistically significant.

In a preferred embodiment, the decreased level of expression or activity of the gene selected from NID2, TJP2, TWIST1, TNFRSF25, BMP7, RUNX3, CCNA1, APC, LOXL1, TUBB4, NTRK2, ARFGAP3, PDLIM4, RASSF1A and OSMR is determined with reference to a control sample. This control sample is preferably taken from normal (i.e. non tumorigenic) tissue in the subject, where expression of the gene selected from NID2, TJP2, TWIST1, TNFRSF25, BMP7, RUNX3, CCNA1, APC, LOXL1, TUBB4, NTRK2, ARFGAP3, PDLIM4, RASSF1A and OSMR is normal. Additionally or alternatively control samples may also be utilised in which there is known to be a lack of expression of the concerned gene. Suitable additional controls may also be included to ensure that the test is working properly, such as measuring levels of expression or activity of a suitable reference gene in both test and control samples.

Expression of a nucleic acid in a test sample can be measured at the RNA level or at the protein level. Methods employing nucleic acid probe hybridization to the relevant transcript(s) of a gene selected from NID2, TJP2, TWIST1, TNFRSF25, BMP7, RUNX3, CCNA1, APC, LOXL1, TUBB4, NTRK2, ARFGAP3, PDLIM4, RASSF1A and OSMR may be employed for measuring the presence and/or level of mRNA. Such methods include use of nucleic acid probe arrays (microarray technology) and Northern blots. Advances in genomic technologies now permit the simultaneous analysis of thousands of genes, although many are based on the same concept of specific probe-target hybridization. Sequencing-based methods are an alternative. These methods started with the use of expressed sequence tags (ESTs), and now include methods based on short tags, such as serial analysis of gene expression (SAGE) and massively parallel signature sequencing (MPSS). Differential display techniques provide yet another means of analyzing gene expression; this family of techniques is based on random amplification of cDNA fragments generated by restriction digestion, and bands that differ between two tissues identify cDNAs of interest.

In a preferred embodiment, the levels of expression of the gene selected from NID2, TJP2, TWIST1, TNFRSF25, BMP7, RUNX3, CCNA1, APC, LOXL1, TUBB4, NTRK2, ARFGAP3, PDLIM4, RASSF1A and OSMR are determined using reverse transcriptase polymerase chain reaction (RT-PCR). RT-PCR is a well known technique in the art which relies upon the enzyme reverse transcriptase to reverse transcribe mRNA to form cDNA, which can then be amplified in a standard PCR reaction. Protocols and kits for carrying out RT-PCR are extremely well known to those of skill in the art and are commercially available.

RT-PCR can be carried out in a non-quantitative manner. End-point RT-PCR measures changes in expression levels using three different methods: relative, competitive and comparative. These traditional methods are well known in the art. Alternatively, RT-PCR is carried out in real time and in a quantitative manner. Real time quantitative RT-PCR has been thoroughly described in the literature and a variety of techniques are possible. Examples include use of Taqman, Molecular Beacons, Scorpion, Plexor and Amplifluor systems as already discussed. All of these systems are commercially available and well characterised, and may allow multiplexing. As mentioned, PCR is a preferred amplification method, but variants on the basic technique and other amplification techniques are also included within the scope of the invention.

Suitable methods for determining expression of the gene selected from NID2, TJP2, TWIST1, TNFRSF25, BMP7, RUNX3, CCNA1, APC, LOXL1, TUBB4, NTRK2, ARFGAP3, PDLIM4, RASSF1A and OSMR at the protein level are also well known to one of skill in the art. Examples include western blots, immunohistochemical staining and immunolocalization, immunofluorescene, enzyme-linked immunosorbent assay (ELISA), immunoprecipitation assays, complement fixation assay, agglutination reactions, radioimmunoassay, flow cytometry, mass spectrofotometry, and equilibrium dialysis. These methods generally depend upon a reagent specific for identification of the gene product from a gene selected from NID2, TJP2, TWIST1, TNFRSF25, BMP7, RUNX3, CCNA1, APC, LOXL1, TUBB4, NTRK2, ARFGAP3, PDLIM4, RASSF1A and OSMR. The reagent is preferably an antibody and may comprise monoclonal or polyclonal antibodies. Fragments and derivative antibodies may also be utilised, to include without limitation Fab fragments, ScFv, single domain antibodies, nanoantibodies, heavy chain antibodies, aptamers etc. . . . which retain gene product binding function. Any detection method may be employed in accordance with the invention. The nature of the reagent is not limited except that it must be capable of specifically identifying the appropriate gene product.

Of course, in the case of a positive diagnosis of cancer, there will be reduced levels or none of the relevant the protein coded by at least one gene selected from NID2, TJP2, TWIST1, TNFRSF25, BMP7, RUNX3, CCNA1, APC, LOXL1, TUBB4, NTRK2, ARFGAP3, PDLIM4, RASSF1A and OSMR. In one embodiment this will present a negative result. In this case, use of suitable controls ensures that false diagnoses will not be made, for example caused by degraded or non-specific reagents. Thus, the same reagent can be tested on samples in which it is known that the at least one gene selected from NID2, TJP2, TWIST1, TNFRSF25, BMP7, RUNX3, CCNA1, APC, LOXL1, TUBB4, NTRK2, ARFGAP3, PDLIM4, RASSF1A and OSMR is expressed. A positive result in this control sample, combined with a negative result in the test sample provides a confident diagnosis of cancer and removes any doubt over the quality of the reagent.

Measurement of expression of a gene on its own does not indicate that the silencing is epigenetic, as the mechanism of silencing could be genetic, for example, by somatic mutation. Additional treatment with reagents such as DAC (5'-deazacytidine), TSA or other treatment affecting epigenetic mechanisms present in cell lines may be included in order to determine that the silencing of the gene is epigenetic. Typically, expression is reactivated or reversed upon treatment with such reagents, indicating that the silencing is epigenetic.

Following diagnosis, treatment is often decided according to the stage of a cancer. The "stage" of a cancer is a descriptor (usually numbers I to IV) of how much the cancer has spread. The stage often takes into account the size of a tumor, how deep it has penetrated, whether it has invaded adjacent organs, if and how many lymph nodes it has metastasized to, and whether it has spread to distant organs. Staging of cancer is important because the stage at diagnosis is the biggest predictor of survival, and treatments are often changed based on the stage. For instance, approximately 70% to 80% of patients diagnosed with bladder cancer will present with superficial bladder tumors (stage Ta, Tis, or T1). Tis tumors, also referred to as CIS (carcinoma in situ), are flat tumors confined to the urothelium but, if left untreated, will likely progress to muscle invasive disease. Tumors that are T2 and T3 are indicative of invasion into the bladder muscle or fat. Stage 4 tumors represent those that have invaded the pelvic or abdominal wall or have metastasized to adjacent organs.

The methylation status and/or expression level of the gene selected from NID2, TJP2, TWIST1, TNFRSF25, BMP7, RUNX3, CCNA1, APC, LOXL1, TUBB4, NTRK2, ARFGAP3, PDLIM4, RASSF1A and OSMR can be correlated to the stage of cancer. The experimental section provides evidence on methylation of certain genes selected from NID2, TJP2, TWIST1, TNFRSF25, BMP7, RUNX3, CCNA1, APC, LOXL1, TUBB4, NTRK2, ARFGAP3, PDLIM4, RASSF1A and OSMR to occur at early stage of cancer. Methylation changes that develop early in the process of carcinogenesis are not only ideal for screening purposes, but also interesting targets for monitoring staging and the state of the disease and/or monitoring progression or outcome of the disease, checking for recurrence of disease following treatment. Thus, the marker is particularly useful in a method of prognosis to cancer comprising detecting epigenetic silencing of at least one gene selected from NID2, TJP2, TWIST1, TNFRSF25, BMP7, RUNX3, CCNA1, APC, LOXL1, TUBB4, NTRK2, ARFGAP3, PDLIM4, RASSF1A and OSMR, wherein epigenetic silencing of the gene is indicative for cancer development. Related hereto, the invention also provides for a method for determining the stage of cancer comprising determining epigenetic silencing of a gene selected from NID2, TJP2, TWIST1, TNFRSF25, BMP7, RUNX3, CCNA1, APC, LOXL1, TUBB4, NTRK2, ARFGAP3, PDLIM4, RASSF1A and OSMR. In one embodiment, the subject is developing or at risk for developing AJCC stage I, II, III or IV cancer. In this method, a sample is obtained from a subject suffering from or suspected of suffering from cancer. In all these embodiments, epigenetic silencing is detected by determination of the methylation status and/or measurement of expression levels of at least one gene selected from NID2, TJP2, TWIST1, TNFRSF25, BMP7, RUNX3, CCNA1, APC, LOXL1, TUBB4, NTRK2, ARFGAP3, PDLIM4, RASSF1A and OSMR.

All methods of present invention are preferentially used in connection to bladder cancer. To attain high rates of tumor detection, it may be necessary to complement the methods of the invention with established methods for bladder cancer identification. Non-invasive methods may be especially suitable for use in combination with the non-invasive methods of the invention. Methods of present invention are preferentially used in conjunction with one or more of the following methods:

Urinalysis

Urine cytology (microscopic exam of urine to look for cancerous cells)

Cystoscopy (use of lighted instrument to view inside of bladder. Diagnosis and staging of bladder cancer begins with cystoscopy)

Bladder biopsy (usually performed during cystoscopy)

Intravenous pyelogram—IVP (Dyes are injected into the bloodstream, which allow for better visualization of any tumors or abnormalities in the bladder using routine X-rays.)

Imaging Techniques: X-ray imaging of the upper urinary tract (including the ureters and kidneys) may be done to rule out any involvement of these structures. Ultrasound can be used to study the kidneys and a CT scan is often very good at studying the entire length of the urinary tract.

More recently, urine-based marker tests are being developed and provide yet another means to complement the methods of the invention. These new tests are non-invasive and accurate in detecting low-grade bladder cancer and therefore are especially useful in monitoring for recurrence. They comprise:

BTA assays (Polymedco, formerly Bard Diagnostics, USA) detects hCFHrp, or human complement factor H-related protein, which is present in the urine of patients with bladder cancer. There are both quantitative and qualitative BTA methods available.

The NMP22 Test Kit (Matritech Inc., Newton, Mass.) detects a nuclear mitotic apparatus (NMA) protein that is abundant in the nuclear matrix. In bladder tumor cells, NMA is elevated and released in detectable levels. There are both quantitative and qualitative NMP22 methods.

The Vysis UroVysion assay (Abbott Molecular Diagnostics) combines urine cytology with molecular (DNA-based) technology to detect the recurrence of cancer. It employs Fluorescence in situ Hybridization (FISH) technology, which uses small, fluorescent-labeled DNA probes to microscopically identify specific regions of DNA.

ImmunoCyt (DiagnoCure) is an immunocytochemistry assay for the detection of Mucin and CEA antigens expressed by tumor cells in the urine of patients previously diagnosed with bladder cancer. This immunofluoresence method is to be combined with urine cytology for the early detection of bladder cancer recurrence. ImmunoCyt is a qualitative assay.

The targeting of multiple DNA alterations may augment efficient cancer identification. Therefore, additional genetic markers may be used in order to supplement the methods of the invention. The genetic markers may concern mutation markers that allow detection of mutations in distinct genes, or, alternatively epigenetic markers that allow detection of DNA methylation in distinct genes.

As discussed herein, a combination of the methods of the invention with (urinary) cytology and/or FGFR3 mutation analysis has been shown to markedly enhance the sensitivity associated with both cytology and mutation analysis whilst retaining specificity. Thus, in general terms the invention provides for enhancement of bladder cancer detection through a combination of determining the methylation status of relevant genes and cytology and/or mutation analysis. The methods of the invention may be utilised in combination with urinary cytology and/or mutation analysis in certain embodiments. In specific embodiments the mutation analysis comprises, consists essentiality of or consists of fibroblast growth factor receptor 3 (FGFR3) mutation analysis. FGFR3 mutations have been reported as being very frequent in bladder tumours of low stage and grade. Methods including detecting mutation in FGFR3 may thus be utilised to diagnose, predict etc. superficial or early stage bladder cancer in certain embodiments. Any suitable mutational analysis technique may be employed. In specific embodiments, identification of one or more single nucleotide mutations in the FGFR3 gene is carried out. This may be carried out through use of suitable primer extension assays, such as described by Van Oers et al (Clinical Cancer Research 2005, 11 (21) Nov. 1, 2005) which reference is incorporated herein in its entirety. Primers for use in these methods are set forth as follows:

5'-T$_{46}$CGTCATCTGCCCCCACAGAG-3'  SEQ ID NO: 49

5'-T$_{36}$TCTGCCCCCACAGAGCGCT-3'  SEQ ID NO: 50

5'-T$_{28}$TCTGCCCCCACAGAGCGCT-3'  SEQ ID NO: 51

5'-T$_{29}$GGTGGAGGCTGACGAGGCG-3'  SEQ ID NO: 52

5'-T$_{43}$ACGAGGCGCGGCAGTGTGT-3'  SEQ ID NO: 53

5'-T$_{34}$CCTGTTCATCCTGGTGGTGG-3'  SEQ ID NO: 54

5'-T$_{50}$GCACAACCTCGACTACTACAAG-3'  SEQ ID NO: 55

5'-T$_{20}$CACAACCTCGACTACTACAAGA-3'  SEQ ID NO: 56

Thus, the following mutations may be identified: R248C, S249C, G372C, Y375C, A393E, K652E/Q, K652M/T, as shown in the table below. The methods may employ multiplex PCR followed by single nucleotide primer extension using labelled dideoxynucleotides.

cially preferred is use of the three gene panel, NID2, TWIST1 and RUNX3 in combination with urinary cytology and/or FGFR3 mutation analysis.

Preferably the at least one gene selected from NID2, TJP2, TWIST1, TNFRSF25, BMP7, RUNX3, CCNA1, APC, LOXL1, TUBB4, NTRK2, ARFGAP3, PDLIM4, RASSF1A and OSMR is combined with at least two other genes involved in the establishment of (bladder) cancer. Preferably the at least one gene selected from NID2, TJP2, TWIST1, TNFRSF25, BMP7, RUNX3, CCNA1, APC, LOXL1, TUBB4, NTRK2, ARFGAP3, PDLIM4, RASSF1A and OSMR is combined with and at least three, four, five or six other genes involved in the establishment of cancer. Any gene involved in the establishment of bladder cancer may be utilized in combination with the selected gene in the method of present invention.

Testing can be performed diagnostically or in conjunction with a therapeutic regimen. Epigenetic loss of function of at least one gene selected from NID2, TJP2, TWIST1, TNFRSF25, BMP7, RUNX3, CCNA1, APC, LOXL1, TUBB4, NTRK2, ARFGAP3, PDLIM4, RASSF1A and OSMR can be rescued by the use of DNA demethylating agents and/or DNA methyltransferase inhibitors. Testing can be used to determine what therapeutic or preventive regimen to employ on a patient and be used to monitor efficacy of a therapeutic regimen.

Accordingly, also provided is a method for predicting the likelihood of successful treatment of bladder cancer with a DNA demethylating agent and/or a DNA methyltransferase

| Primer | SEQ ID NO. | Sequence | Strand | Primer Extension Wild-type | Mutant | Concentration (pmol/µL) |
|---|---|---|---|---|---|---|
| R248C | SEQ ID NO: 49 | 5'-T$_{46}$CGTCATCTGCCCCCACAGAG-3' | sense | C | T | 2.0 |
| S249C | SEQ ID NO: 50 | 5'-T$_{36}$TCTGCCCCCACAGAGCGCT-3' | sense | C | G | 1.2 |
| S249C | SEQ ID NO: 51 | 5'-T$_{28}$TCTGCCCCCACAGAGCGCT-3' | sense | C | G | 1.2 |
| G372C | SEQ ID NO: 52 | 5'-T$_{29}$GGTGGAGGCTGACGAGGCG-3' | sense | G | T | 0.4 |
| Y375C | SEQ ID NO: 53 | 5'-T$_{43}$ACGAGGCGCGGCAGTGTGT-3' | sense | A | G | 0.6 |
| A393E | SEQ ID NO: 54 | 5'-T$_{34}$CCTGTTCATCCTGGTGGTGG-3' | sense | C | A | 2.4 |
| K652E/Q | SEQ ID NO: 55 | 5'-T$_{50}$GCACAACCTCGACTACTACAAG-3' | sense | A | G/C | 1.2 |
| K652M/T | SEQ ID NO: 56 | 5'-T$_{20}$CACAACCTCGACTACTACAAGA-3' | sense | A | T/C | 0.8 |

Other molecular markers may be additionally or alternatively investigated, such as Ki-67 labelling (MIB-1 staining).

In certain embodiments of the methods of the invention, the methylation status of at least one gene selected from NID2, TJP2, TWIST1, TNFRSF25, BMP7, RUNX3, CCNA1, APC, LOXL1, TUBB4, NTRK2, ARFGAP3, PDLIM4, RASSF1A and OSMR is analysed in combination with at least one other gene involved in the establishment of cancer, in particular bladder cancer.

Panels of two, three, four, five, six etc. up to all of the genes listed are also envisioned, as discussed herein. Espeinhibitor and/or HDAC inhibitor comprising detecting an epigenetic change in at least one gene selected from NID2, TJP2, TWIST1, TNFRSF25, BMP7, RUNX3, CCNA1, APC, LOXL1, TUBB4, NTRK2, ARFGAP3, PDLIM4, RASSF1A and OSMR, wherein detection of the epigenetic change is indicative that the likelihood of successful treatment is higher than if the epigenetic modification is not detected.

Alternatively, the method comprises measurement of expression levels of the gene selected from NID2, TJP2, TWIST1, TNFRSF25, BMP7, RUNX3, CCNA1, APC, LOXL1, TUBB4, NTRK2, ARFGAP3, PDLIM4, RASSF1A and OSMR, wherein a reduced level of expression indicates the likelihood of successful treatment of cancer is higher than if the gene is expressed at a higher level.

Alternatively, the invention provides for a method for predicting the likelihood of resistance to treatment of bladder cancer with a DNA demethylating agent and/or DNA methyltransferase inhibitor and/or HDAC inhibitor comprising detecting an epigenetic change in at least one gene selected from NID2, TJP2, TWIST1, TNFRSF25, BMP7, RUNX3, CCNA1, APC, LOXL1, TUBB4, NTRK2, ARFGAP3, PDLIM4, RASSF1A and OSMR, wherein detection of the epigenetic change is indicative that the likelihood of resistance to treatment is lower than if the epigenetic modification is not detected. Alternatively, the method comprises measurement of expression levels of the gene selected from NID2, TJP2, TWIST1, TNFRSF25, BMP7, RUNX3, CCNA1, APC, LOXL1, TUBB4, NTRK2, ARFGAP3, PDLIM4, RASSF1A and OSMR, wherein a higher level of expression indicates the likelihood of resistance to treatment of cancer is higher than if the gene is expressed at a reduced level.

Epigenetic loss of gene function can identify the need for treatment which may differ according to the type of carcinoma. Therefore, the present invention also relates to a method of selecting a suitable treatment regimen for bladder cancer comprising detecting an epigenetic change in at least one gene selected from NID2, TJP2, TWIST1, TNFRSF25, BMP7, RUNX3, CCNA1, APC, LOXL1, TUBB4, NTRK2, ARFGAP3, PDLIM4, RASSF1A and OSMR, wherein detection of the epigenetic change results in selection of a DNA demethylating agent and/or a DNA methyltransferase inhibitor and/or a HDAC inhibitor for treatment and wherein if the epigenetic change is not detected, a DNA demethylating agent and/or a DNA methyltransferase inhibitor and/or a HDAC inhibitor is not selected for treatment.

In certain aspects, epigenetic loss of gene function can identify the need for treatment. Accordingly, the invention provides a method for predicting suitable treatment of a transitional cell carcinoma or squamous cell carcinoma obtained from a subject, comprising determining the methylation status of at least one gene selected from NID2, TJP2, TWIST1, TNFRSF25, BMP7, RUNX3, CCNA1, APC, LOXL1, TUBB4, NTRK2, ARFGAP3, PDLIM4, RASSF1A and OSMR, in a transitional cell tumor, wherein if at least one gene is methylated, in particular hypermethylated, the need for resection of the transitional cell carcinoma is identified. In such case, preventive treatment may be recommended and involve resection of the transitional cell carcinoma.

Alternatively, the invention provides for a method for predicting suitable treatment of a transitional cell carcinoma or squamous cell carcinoma obtained from a subject, comprising determining the methylation status at least one gene selected from NID2, TJP2, TWIST1, TNFRSF25, BMP7, RUNX3, CCNA1, APC, LOXL1, TUBB4, NTRK2, ARFGAP3, PDLIM4, RASSF1A and OSMR, in a transitional cell tumor, wherein if the at least one gene is unmethylated or methylated to a lesser degree, it is decided that there is no need for resection of the transitional cell tumor. For the avoidance of doubt, all embodiments of the invention apply to these latter aspects.

In a further related aspect, the invention provides a method of treating bladder cancer in a subject comprising administration of a DNA demethylating agent and/or a DNA methyltransferase inhibitor wherein the subject has been selected for treatment on the basis of a method of the invention.

The invention also provides kits which may be used in order to carry out the methods of the invention. The kits may incorporate any of the preferred features mentioned in connection with the various methods (and uses) of the invention herein.

Thus, a kit is provided for detecting a predisposition to, or the incidence of, bladder cancer in a sample comprising at least one primer pair (as defined herein) for determining the methylation status of each of NID2, TWIST1 and RUNX3. As discussed herein, this panel of genes has been shown to be useful in predicting or diagnosing bladder cancer, non-invasively, with excellent sensitivity and specificity. Suitable primer pairs for determining the methylation status of each of NID2, TWIST1 and RUNX3 are described herein and may comprise the nucleotide sequences set forth as SEQ ID NO 40 and 41 (NID2), 22 and 23 (TWIST1) and 31 and 32 (RUNX3). The primers may permit direct determination of the methylation status of the panel of genes, for example following bisulphite treatment of the DNA. Thus, they may be MSP or bisulphite sequencing primers for example. The kits may additionally include one or more probes for real-time or end-point detection. Suitable probes comprise the nucleotide sequences set forth as SEQ ID NO: 42 (NID2), 24 (TWIST1) and 33 (RUNX3). The probes may additionally or alternatively permit direct determination of the methylation status of the panel of genes, for example following bisulphite treatment of the DNA. Blocking probes may also be utilised in certain embodiments, according to the Heavymethyl technique (see Nucleic Acids Res. 2004; 32(i) e10).

The kit may further comprise means for processing a sample, in particular a sample including bladder cells or genomic DNA from bladder cells such as a suitable tissue or urine sample, as discussed herein.

A kit is also provided for detecting a predisposition to, or the incidence of, bladder cancer in a sample comprising:
(a) means for detecting an epigenetic change in at least one gene selected from NID2, TJP2, TWIST1, TNFRSF25, BMP7, RUNX3, CCNA1, APC, LOXL1, TUBB4, NTRK2, ARFGAP3, PDLIM4, RASSF1A and OSMR, in particular TWIST1
(b) means for processing a sample.

The sample for processing comprises, consists essentially, or consists of a tissue sample and/or a bladder tissue sample and/or a urine sample.

The kit preferably comprises means for detecting an epigenetic change in a panel of genes comprising at least two, three, four or five of the genes from NID2, TJP2, TWIST1, TNFRSF25, BMP7, RUNX3, CCNA1, APC, LOXL1, TUBB4, NTRK2, ARFGAP3, PDLIM4, RASSF1A and OSMR, wherein detection of an epigenetic change in at least one of the genes in the panel is indicative of a predisposition to, or the incidence of, bladder cancer.

Preferably, the kit detects an epigenetic change in a panel of genes comprising NID2 and/or BMP7. In certain embodiments, the panel of genes comprises, consists essentially of or consists of NID2 and BMP7, NID2, TJP2 and BMP7, NID2, TNFRSF25 and BMP7 or NID2, BMP7, TWIST1, CCNA1 and RUNX3. A most preferred three gene panel comprises, consists essentially of or consists of NID2, TWIST1 and RUNX3. Preferably, the kit enables the detection to be carried out in a single reaction. Preferably, the epigenetic change is methylation.

This kit is preferably a kit for use in MSP and even more preferably a real-time detection version of MSP. In one embodiment the kit permits an end-point detection version of MSP to be carried out.

In certain embodiments, the kit of the invention comprises a reagent which modifies unmethylated cytosine (but not methylated cytosine) or vice versa. In a preferred embodiment, the reagent comprises bisulphite, preferably sodium bisulphite but may comprise hydrazine for example.

The kit may also include suitable primers for determining whether the at least one gene selected from NID2, TJP2, TWIST1, TNFRSF25, BMP7, RUNX3, CCNA1, APC, LOXL1, TUBB4, NTRK2, ARFGAP3, PDLIM4, RASSF1A and OSMR is methylated. These primers may comprise any of the primers discussed in detail in respect of the various methods of the invention which may be employed in order to determine the methylation status of the relevant (at least one) gene, and variants thereof.

The kit may further comprise probes for real-time detection of amplification products. The probes may comprise any suitable probe type for real-time detection; non-limiting examples include use of TAQMAN probes and/or MOLECULAR BEACONS probes and/or AMPLIFLUOR primers and/or FRET probes and/or SCORPION primers and/or oligonucleotide blockers. Such kits for real-time detection may also be used for end-point detection.

The primers and/or probes may permit direct determination of the methylation status of the at least one gene, for example following bisulphite treatment of the (DNA in the) sample, as discussed herein.

In specific embodiments, the primers and/or probes in the kit are selected from those which comprise, consist essentially of, or consist of primers and/or probes comprising, consisting essentially of, or consisting of the following nucleotide sequences for the purposes of amplifying methylated or unmethylated DNA (following bisulphite treatment):

```
S = sense primer
A = antisense primer
MB = molecular beacon

RASSF1A_S (SEQ ID NO. 1):
GCGTTGAAGTCGGGGTTC

RASSF1A_AS (SEQ ID NO. 2):
CCCGTACTTCGCT2AACTTTAAACG

RASSF1A_MB (SEQ ID NO. 3):
5'-FAM-CGTCTGCGTGGTTTCGTTCGGTTCGCGTTTGTTAGGCAGACG-3'-DABCYL

APC(2)_S (SEQ ID NO. 4):
TAT TGC GGA GTG CGG GTC

APC(2)_AS (SEQ ID NO. 5):
TCG ACG AAC TCC CGA CGA

APC(2)_MB (SEQ ID NO. 6):
5'-FAM-CGACATGCGTGTAATTCGTTGGATGCGGATTAGGGCGGCATGTCG-3'-DABCYL

CCNA1_gron_S (SEQ ID NO. 7):
GTTATGGCGATGCGGTTTC

CCNA1_gron_AS (SEQ ID NO. 8):
CCAACCTAAAAAACGACCGA

CCNA1_gron_MB (SEQ ID NO. 9):
5'-FAM-CGACATGCACGACGCCCCCGAACCTAACGCATGTCG-3'-DABCYL

TNERSF25_1_S (SEQ ID NO. 10):
GTCGTCGAGAAGGGTTCGTTT

TNERSF25_1_AS (SEQ ID NO. 11):
GCGTATTCTACTTAACCTATCCGC

TNERSF25_1_MB (SEQ ID NO. 12):
5'-FAM-CGACATGCACGACCCCGCCTCCCCCCGCCGCATGTCG-3'-DABCYL

TUBB4_2_S (SEQ ID NO. 13):
TAAATTAGATCGTCGTTTCGGAG

TUBB4_2_AS (SEQ ID NO. 14):
TACCTCAATTTCTCGATCCGC

TUBB4_2_MB (SEQ ID NO. 15):
5'-FAM-CGACATGCTGGGAGGGTTCGCGGTTATTGTAAGGAGCATGTCG-3'-DABCYL

NTRK2_1_M_S (SEQ ID NO. 16):
GTTAGAGCGCGTTTTTAGCGT

NTRK2_1_M_AS (SEQ ID NO. 17):
CCGCAATACCTAACACTTCCG

NTRK2_1_MB (SEQ ID NO. 18)
5'-FAM-CGACATGCCCGACACGCTCCGAAACACCAGCATGTCG-3'-DABCYL

OSMR_1_S (SEQ ID NO. 19):
GTGTTAAGAGTGCGTAGTAAGACG

OSMR_1_AS (SEQ ID NO. 20):
GAAACGAACGTACAAAAACGA

OSMR_1_MB (SEQ ID NO. 21):
5'-FAM-CGACATGCCGAAACTATAAATCAACTACGAAACAAACGCGCATGTCG-3'-DABCYL

TWIST1_3_S (SEQ ID NO. 22)
GTTAGGGTTCGGGGGCGTTGTT

TWIST1_3_AS (SEQ ID NO. 23):
CCGTCGCCTTCCTCCGACGAA

TWIST1_3_MB (SEQ ID NO. 24):
5'-FAM-CGACATGCCGGCGGGGAAGGAAATCGTTTCGCATGTCG-3'-DABCYL

LOXL1_29309_S (SEQ ID NO. 25):
TAGAGTACGTGTCGGTCGGAT

LOXL1_29309_AS (SEQ ID NO. 26):
ACAAAAACAAAAACGACGCCT

MB_LOXL1_29309b (SEQ ID NO. 27)
5'-FAM-CGACATGCCGGGTGTTGTTGGTCGGCGCGCATGTCG-3'-DABCYL

TJP2_25301_S (SEQ ID NO. 28):
GAGATCGCGGGTTTTATTTC

TJP2_25301_AS (SEQ ID NO. 29):
CCAACTTCCTACGACGCAT

TJP2_25301_MB (SEQ ID NO. 30):
5'-FAM-CGACATGCCTCCCAACCGCGCGACACAAGCATGTCG-3'-
```

-continued

DABCYL

Runx3_3_M_S (SEQ ID NO. 31):
CGTAGGGTTGTATTTGAGCGA

Runx3_3_M_AS (SEQ ID NO. 32):
TAACTTTTAACGAAATTACCCCG

RUNX3_3_MB2 (SEQ ID NO. 33):
5'-FAM-CGACATGCCGGGTTAGGGGGGCGTAAAATTTTATTCGTTGCAT

GTCG-3'-DABCYL

PDLIM4_4_M_S (SEQ ID NO. 34):
GGCGTTTAGGTTAATTTTTCGT

PDLIM4_4_M_AS (SEQ ID NO. 35):
CGATCCCATATCTAAAACCGA

PDLIM4_4_MB (SEQ ID NO. 36):
5'-FAM-CGACATGCCTCGCGATCCGCCCGAAACGCATGTCG-3'-

DABCYL

BMP7_17911_S (SEQ ID NO. 37):
AGCGTAGAGATAGGTTGGTAACG

BMP7_17911_AS (SEQ ID NO. 38):
AAAACGATAACCCTTAAACCGA

MB_BMP7_17911 (SEQ ID NO. 39):
5'-FAM-CGACATGCGCGGAGGGGTTAGCGTGGTTGCATGTCG-3'-

DABCYL

NID2_9091_S (SEQ ID NO. 40):
GCGGTTTTTAAGGAGTTTTATTTTC

NID2_9091_AS (SEQ ID NO. 41):
CTACGAAATTCCCTTTACGCT

MB_NID2_9091 (SEQ ID NO. 42):
5'-FAM-CGACATGGGTTCGTAAGGTTTGGGGTAGCGGCCATGTCG-3'-

DABCYL

ARFGAP3_25342_S (SEQ ID NO. 43):
GCGTTAAGGTACGGGTTTTTC

ARFGAP3_25342_A (SEQ ID NO. 44):
GCCATTTCGCCTAACGAAC

ARFGAP3_25342_MB (SEQ ID NO. 45):
5'-FAM-CGACATGCACGCGCCCTCCTTCGACACGCATGTCG-3'-

DABCYL

β-Actin_S (SEQ ID NO. 46):
TAGGGAGTATATAGGTTGGGGAAGTT?

β-Actin_A (SEQ ID NO. 47):
AACACACAATAACAAACACAAATTCAC

β-Actin_MB (SEQ ID NO. 48):
5'-FAM-CGACTGCGTGTGGGGTGGTGATGGAGGAGGTTTAGGCAGTCG-

3'-DABCYL

The labels indicated are optional. FAM and DABCYL are representative examples of fluorescent markers which can participate in FRET to provide a reliable indicator of amplification, as discussed herein. Other fluorophores and quenchers may be employed, in particular as FRET pairs, as desired and as would be appreciated by a skilled person.

As discussed, suitable controls may be utilised in order to act as quality control for the methods and be included in the kit of the invention. One example of a suitable internal reference gene, which is generally unmethylated, but may be treated so as to be methylated, is β-actin. The kit of the invention may further comprise primers for the amplification of a control nucleic acid which may comprise at least one gene selected from NID2, TJP2, TWIST1, TNFRSF25, BMP7, RUNX3, CCNA1, APC, LOXL1, TUBB4, NTRK2, ARFGAP3, PDLIM4, RASSF1A and OSMR in unmethylated and/or methylated form.

The kits of the invention may additionally include suitable buffers and other reagents for carrying out the claimed methods of the invention. In one embodiment, the kit of the invention further comprises, consists essentially of, or consists of nucleic acid amplification buffers.

The kit may also additionally comprise, consist essentially of or consist of enzymes to catalyze nucleic acid amplification. Thus, the kit may also additionally comprise, consist essentially of or consist of a suitable polymerase for nucleic acid amplification. Examples include those from both family A and family B type polymerases, such as Taq, Pfu, Vent etc.

As indicated herein above, the kit may comprise means for processing a urine sample. Such means for processing a urine sample may comprise a stabilising buffer and/or reagents for extraction/isolation/concentration/purification of DNA. The kit may also incorporate a sealable vessel for collection of a urine sample.

The various components of the kit may be packaged separately in separate compartments or may, for example be stored together where appropriate.

The kit may also incorporate suitable instructions for use, which may be printed on a separate sheet or incorporated into the kit packaging for example.

The kits of the invention may also incorporate means for detecting mutations in the FGFR3 gene. As discussed above, mutations in this gene are linked to the incidence of bladder cancer and thus complement, in synergistic fashion, the methods of the invention. The means for detecting appropriate mutations may comprise suitable primers, such as those selected from primers comprising, consisting essentially of or consisting of the nucleotide sequences set forth as SEQ ID NO's 49 to 56. These kits may also incorporate other components such as dideoxynucleotides and/or primers for amplifying regions of exons 7, 10 and 15 of the FGFR3 gene, as discussed on page 7744 of Van Oers et al (incorporated herein by reference).

The invention will now be described with respect to the following non-limiting examples.

DESCRIPTION OF THE FIGURES

FIG. 5A: ROC curve for the individual gene TWIST1 (sensitivity 76.8%, specificity 96.8%)

FIG. 5B: ROC curve for the individual gene RUNX3 (sensitivity 57.1%, specificity 98.4%)

FIG. 5C: ROC curve for the individual gene NID2 (sensitivity 75.0%, specificity 88.9%)

FIG. 5D: ROC curve for the combination of TWIST1, RUNX3 and NID2 genes (sensitivity 89.3%, specificity 92.1%). The area under the curve (AUC) is 0.919. The 95% CI range was 0.870 to 0.995 at a significance of P=0.0001 for area=5.

EXPERIMENTAL SECTION

Example 1

Figure 1:
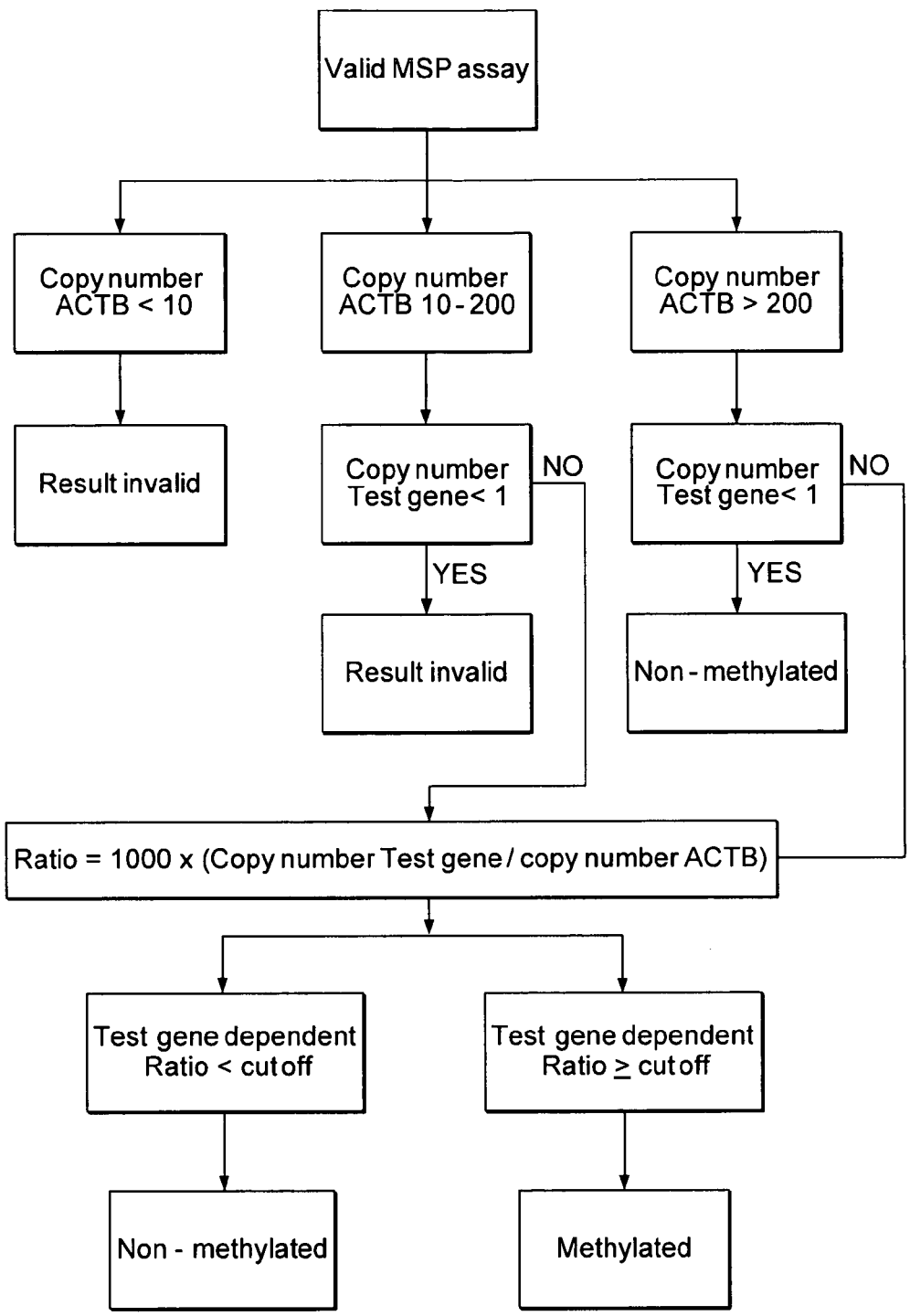
FIG. 1. Decision tree for ratio determination for urine training set 1 (Example 1).

A Real-time MSP Assay for Early Detection of Bladder Cancer—Urine Training Set 1

Materials and Methods

Marker identification: Candidate genes were identified using re-expression profiles of bladder cancer cell lines. Promoter sequences were linked with gene expression to identify valid epigenetically silenced genes. An established pharmacologic unmasking strategy (5-aza-2'-deoxycytidine [DAC] and trichostatin A [TSA]) for re-expression analysis of epigenetically targeted genes was combined with proprietary advanced bioinformatics tools to identify genes prone to promoter methylation.

Marker selection in bladder tissue: Marker candidates identified by re-expression were screened using 74 real-time methylation specific PCR (real-time MSP) assays. These assays were used to assess the methylation status of 59 gene promoters in formalin-fixed paraffin-embedded (FFPE) tissue samples collected from various urological clinics. Samples included 91 carcinomas of various stages and 39 samples from patients with no evidence of cancer. These samples were divided into a training and an independent test sets, and used to select the gene methylation assays best able to discriminate between cancerous and non-cancerous samples.

Urine sample collection: Prospective, randomly collected urine samples from multiple centers in Belgium, UK and The Netherlands were used in the present study. In this trial, symptomatic patients, attending a urology clinic and ultimately diagnosed with bladder cancer or other non-malignant urological disorders, provided a urine sample for use in real-time MSP analysis. Total enrolment is expected to reach 400 individuals within 2 years. From this ongoing trial, 218 urine samples were available for the present study. These samples included 150 samples from patients with no evidence of cancer and 68 samples from patients covering all stages of bladder cancer, with 82% representing early stage disease (see Table 3 for details). An aliquot of these urine samples was used for cytology analysis.

DNA isolation: DNA was isolated from tissue and urine using a standard DNA isolation method and standard equipment. Briefly for urine DNA preparation, Fresh collected urine samples were low-speed centrifuged at 3000 g at room temperature for 10 minutes. The supernatant was separated from the sediment fraction. Both fractions were stored at −20° C. until further processing.

Prior to DNA isolation of the pellet fraction, the frozen sample was thawed at room temperature and centrifuged at 3000 g for 5 minutes to separate the remaining supernatant (few μl) from the cell debris pellet.

Genomic DNA was extracted from the sediment fraction using the PUREGENE® DNA Purification Kit from Gentra. 700 μl of Cell Lysis Solution (provided with kit) was added to the pellet and further processed according to manufacturer's instructions. DNA was rehydrated adding 45 μl of LoTE buffer and was incubated during 1 hour shaking at 65° C. followed by overnight shaking at 20° C.

DNA modification: 1.5 μg of DNA (or the totality if less than 1.5 μg) was subjected to bisulphite modification in 96-wells format on a pipetting robot (Tecan), using the EZ-96DNA Methylation kit (Zymo Research), according to the manufacturer's protocol. Basically, aliquots of 45 μl were mixed with 5 μl of M-Dilution Buffer and incubated at 37° C. for 15 minutes shaking at 1100 rpm. Then 100 μl of the diluted CT Conversion Reagent was added and samples were incubated at 70° C. for 3 hours, shaking at 1100 rpm in the dark. After conversion, the samples were desalted by incubation on ice for 10 minutes and addition of 400 μl of M-Binding buffer. The samples were loaded on a Zymo-Spin I Column in a collection tube and after centrifugation washed with 200 μl of M-Wash Buffer. 200 μl of M-Desulphonation Buffer was put onto the column and incubated at room temperature for 15 minutes. After centrifugation of the columns, they were washed twice with 200 μl of M-Wash Buffer. Finally, the DNA was washed from the column in 50 μl Tris-HCl 1 mM pH8.0 and stored at −80° C., until further processing.

DNA amplification: Real-time MSP was applied on a 7900HT fast real-time PCR system (Applied Biosystems). 2.4 μl of the modified DNA was added to a PCR mix (total volume 12 μl) containing buffer (16.6 mM $(NH_4)_2SO_4$, 67 mM Tris (pH 8.8), 6.7 mM $MgCl_2$, 10 mM β-mercaptoethanol), dNTPs (5 mM), forward primer (6 ng), reverse primer (18 ng), molecular beacon (0.16 μM), and Jumpstart DNA Taq polymerase (0.4 units; Sigma Aldrich). The primer sequences and molecular beacon sequences used for each of the genes are summarized in table 1. Cycle program used was as follows: 5 minutes 95° C., followed by 45 cycles of 30 seconds 95° C., 30 seconds 57° C. (51° C. for APC) (=plateau data-collection), and 30 seconds 72° C. A standard curve ($2 \times 10^6$–20 copies) was included to determine copy numbers of unknown samples by interpolation of their Ct values to the standard curve.

In addition to the bladder test genes, the independent reference gene β-actin (ACTB) was also measured:

β-Actin forward primer
5' - TAGGGAGTATATAGGTTGGGGAAGTT - 3'

β-Actin reverse primer
5' - AACACACAATAACAAACACAAATTCAC - 3' beacon
5'-FAM-CGACTGCGTGTGGGGTGGTGATGGAGGAGGTTTAGGCAGTCG-
3'-DABCYL

The ratios between the bladder test genes and ACTB were calculated to generate the test result. The samples were classified as methylated, non-methylated, or invalid based on the decision tree shown in FIG. 1.

TABLE 1

Primer and beacon sequences (S: sense; AS: anti-sense; MB: molecuar beacon)

| Assay reference | Accession number | Amplicon length (bp) | Primer/Beacon ID | Primer/Beacon sequences (5' - 3') (modification beacons: 5'FAM, 3'DABCYL) |
|---|---|---|---|---|
| RASSF1A | AC002481 | 76 | RASSF1A_S | (SEQ ID NO: 1) GCGTTGAAGTCGGGGTTC |
| | | | RASSF1A_AS | (SEQ ID NO: 2) CCCGTACTTCGCTAACTTTAAACG |
| | | | RASSF1A_MB | (SEQ ID NO: 3) CGTCTGCGTGGTTTCGTTCGGTTC GCGTTTGTTAGGCAGACG |
| APC | NM_000038 | 74 | APC(2)_S | (SEQ ID NO: 4) TATTGCGGAGTGCGGGTC |
| | | | APC(2)_AS | (SEQ ID NO: 5) TCGACCGAACTCCCGACGA |
| | | | APC(2)_MB | (SEQ ID NO: 6) CGACATGCGTTGTGTAATTCGTTG GATGCGGATTAGGGCGGCATGTCG |
| CCNA1 | NM_003914 | 152 | CCNA1_gron_S | (SEQ ID NO: 7) GTTATGGCGATGCGGTTTC |
| | | | CCNA1_gron_AS | (SEQ ID NO: 8) CCAACCTAAAAAACGACCGA |
| | | | CCNA1_gron_MB | (SEQ ID NO: 9) CGACATGCACGACGCCCCCGAACC TAACGCATGTCG |
| TNFRSF23 | NM_148972 | 137 | TNFRSF25_1_S | (SEQ ID NO: 10) GTCGTCGAGAAGGGTTCGTTT |
| | | | TNFRSF25_1_AS | (SEQ ID NO: 11) GCGTATTCTACTTAACCTATCCG C |
| | | | TNFRSF25_1_MB | (SEQ ID NO: 12) CGACATGCACGACCCCGCCTCCC CCCGCCGCATGTCG |
| TUBB4 | NM_006057 | 123 | TUBB4_2_S | (SEQ ID NO: 13) TAAATTAGATCGTCGTTTGGGAG |
| | | | TUBB4_2_AS | (SEQ ID NO: 14) TACCTCAATTTCTCGATCCGC |
| | | | TUBB4_2_MB | (SEQ ID NO: 15) CGACATGCTGGGAGGGTTCGCGG TTATTGTAAGGAGCATGTCG |
| NTRK2_1 | NM_001007097 | 123 | NTRK2_1_M_S | (SEQ ID NO: 16) GTTACAGCGCGTTTTTAGCGT |
| | | | NTRK2_1_M_AS | (SEQ ID NO: 17) CCGCAATACCTAACACTTCCG |
| | | | NTRK2_1_MB | (SEQ ID NO: 18) CGACATGCCCGACACGCTCCGAA ACACCAGCATGTCG |
| OSMR | NM_003999 | 148 | OSMR_1_S | (SEQ ID NO: 19) GTGTTAAGAGTGCGTAGTAAGAC G |
| | | | OSMR_1_AS | (SEQ ID NO: 20) GAAACGAACGTACAAAAACGA |
| | | | OSMR_1_MB | (SEQ ID NO: 21) CGACATGCCGAAACTATAAATCA ACTACGAAACAAACGCGCATGTC C |
| TWIST1 | NM_000474 | 77 | TWIST1_3_S | (SEQ ID NO: 22) GTTAGGGTTCGGGGCGTTGTT |
| | | | TWIST1_3_AS | (SEQ ID NO: 23) CCGTCGCCTTCCTCCGACGAA |
| | | | TWIST1_3_MB | (SEQ ID NO: 24) CGACATGCCGGCGGGGAAGGAAA TCGTTTCGCATGTCG |
| LOXL1 | ENST00000261921 | 132 | LOXL1_29309_S | (SEQ ID NO: 25) TAGAGTACGTGTCGGTCGGAT |
| | | | LOXL1_29309_AS | (SEQ ID NO: 26) ACAAAAACAAAAACGACGCCT |
| | | | MB_LOXL1_29309b | (SEQ ID NO: 27) CGACATGCCGGGTGTTGTTGGTC GGCGCGCATGTCG |
| TJP2 | NM_0004817 | 167 | TJP2_25301_S | (SEQ ID NO: 28) GAGATCGCGGGTTTTTATTTC |
| | | | TJP2_25301_AS | (SEQ ID NO: 29) CCAACTTCCTACGACGCAT |
| | | | TJP2_25301_MB | (SEQ ID NO: 30) CGACATGCCTCCCAACCGCGCGA CACAAGCATGTCG |
| RUNX3 | ENST00000308873 | 127 | Runx3_3_M_S | (SEQ ID NO: 31) CGTAGGGTTGTATTTGAGCGA |
| | | | Runx3_3_M_AS | (SEQ ID NO: 32) TAACTTTTAACGAAATTACCCCG |
| | | | RUNX3_3_MB2 | (SEQ ID NO: 33) CGACATGCCGGGTTAGGGGGCG TAAAATTTTATTCGTTGCATGTC G |
| PDL1M4 | EN3T00000379038 | 95 | PDLIM4_4_M_S | (SEQ ID NO: 34) GGCGTTTAGGTTAATTTTTCGT |
| | | | PDLIM4_4_M_AS | (SEQ ID NO: 35) CGATCCCATATCTAAAACCGA |
| | | | PDLIM4_4_MB | (SEQ ID NO: 36) CGACATGCCTCGCGATCCGCCCG AAACGCATGTCG |
| BMP7 | NM_001719 | 111 | BMP7_17911_S | (SEQ ID NO: 37) AGCGTAGAGATAGGTTGGTAACG |
| | | | BMP7_17911_AS | (SEQ ID NO: 38) AAAACGATAACCCTTAAACCGA |
| | | | MB_BMP7_17911 | (SEQ ID NO: 39) CGACATGCGCGGAGGGGTTAGCG TGGTTGCATGTCG |
| NID2 | NM_007361 | 99 | NID2_9019_S | (SEQ ID NO: 40) GCGGTTTTTAAGGAGTTTTATTT TC |
| | | | NID2_9091_AS | (SEQ ID NO: 41) CTACGAAATTCCCTTTACGCT |
| | | | MB_NID2_9091 | (SEQ ID NO: 42) CGACATGGGTTCGTAAGGTTTGG GGTAGCGGCCATGTCG |

TABLE 1-continued

Primer and beacon sequences (S: sense; AS: anti-sense; MB: molecuar beacon)

| Assay reference | Accession number | Amplicon length (bp) | Primer/Beacon ID | Primer/Beacon sequences (5' - 3') (modification beacons: 5'FAM, 3'DABCYL) |
|---|---|---|---|---|
| ARFGAP3 | NM_014570 | 106 | ARFGAP3_25342_S (SEQ ID NO: 43) | GCGTTAAGGTACGGGTTTTC |
|  |  |  | ARFGAP3_25342_A (SEQ ID NO: 44) | GCCATTTCGCCTAACGAAC |
|  |  |  | ARFGAP3_25342_MB (SEQ ID NO: 45) | CGACATGCACGCGCCCTCCTTCG ACACGCATGTCG |

Results:

Assay validity rate in tissue and urine: One hundred and thirty FFPE and 218 urine samples were processed using real-time MSP (Table 2). The validity rates were based on the criteria shown in FIG. 1. The real-time MSP assays produced valid results in 96% of the FFPE samples and in 94% of the urine samples.

TABLE 2

Summary of samples evaluated by real-time MSP

| Sample sets | Sample types | Sample numbers | Valid tests [%] |
|---|---|---|---|
| Tissue training set | Cancer | 53 | 53/53 [100] |
|  | Controls | 30 | 25/30 [83] |
|  | Total | 83 | 78/83 [94] |
| Tissue Test Set | Cancer | 38 | 38/38 [100] |
|  | Controls | 9 | 9/9 [100] |
|  | Total | 47 | 47/47 [100] |
| Tissue sets Combined | Cancer | 91 | 91/91 [100] |
|  | Controls | 39 | 34/39 [87] |
|  | Total | 130 | 125/130 [96] |
| Uring training set | Cancer | 68 | 62/68 [91] |
|  | Controls | 150 | 143/150 [95] |
|  | Total | 218 | 205/218 [94] |

Figure 2:
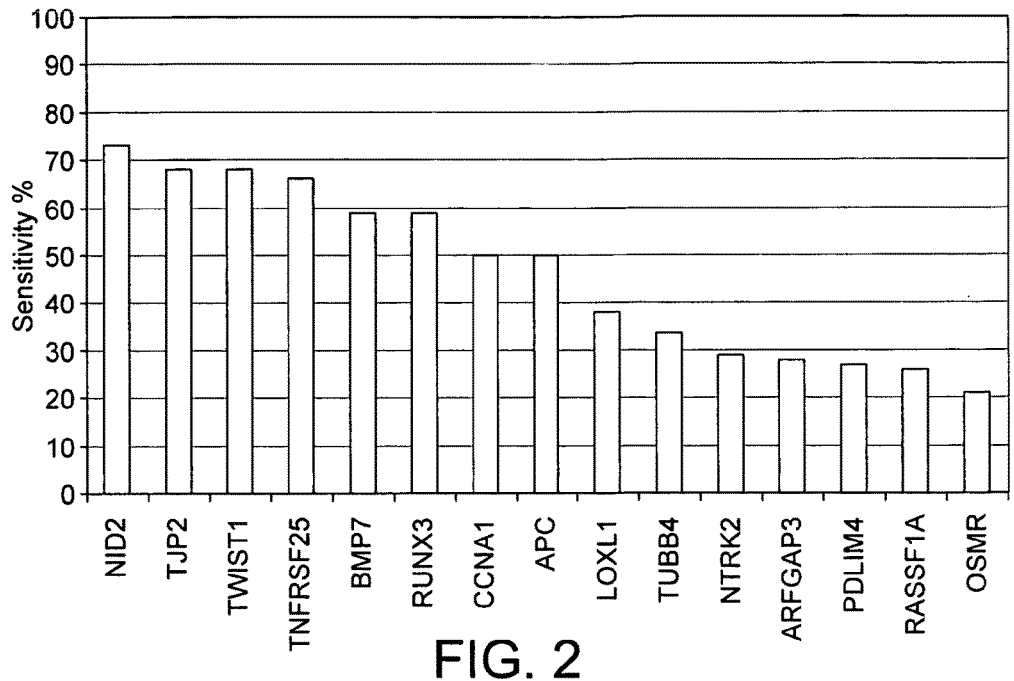
FIG. 2. Individual gene assay performance (sensitivity [%] where the analytical cut-off was set to give 100% specificity) using the tissue test set containing 9 controls (non cancerous disease) and 38 bladder carcinomas for real-time MSP. For the following genes only 22 bladder carcinomas and 7 controls were available for testing: NID2, TJP2, TWIST1, BMP7, RUNX3, ARFGAP3 and PDLIM4.

Marker selection in bladder tissue: Based on re-expression, the 74 most differentially methylated gene sequences were validated on retrospectively collected tumors from 53 bladder cancer patients and 30 histopathologically normal tissue samples using real-time MSP assays. Several markers reliably detected bladder cancer in those tissue samples (data not shown). The results were confirmed on an independent test set containing 9 tissue controls (non cancerous disease) and 38 carcinomas. The individual performance of the 15 best performing tissue markers is shown in FIG. 2, when the analytical cut-off was set to give 100% specificity. Several combinations of the tested markers reliably detected bladder cancer with high specificity and sensitivity (Table 3).

TABLE 3

Performance of several tissue gene panels reliably detected Bladder cancer using real-time MSP. 22 carcinomas and 7 controls were available from the tissue test set for all genes.

|  | Sensitivity % (# positive/# total) | Specificity % (# positive/# total) |
|---|---|---|
| Tissue panel 1: |  |  |
| NID2 TJP2 BMP7 | 100 (22/22) | 100 (0/7) |
| Tissue panel 2: |  |  |
| NID2 TNFRSF25 BMP7 | 100 (22/22) | 100 (0/7) |
| Tissue panel 3: |  |  |
| NID2 BMP7 | 91 (20/22) | 100 (0/7) |

Figure 3:
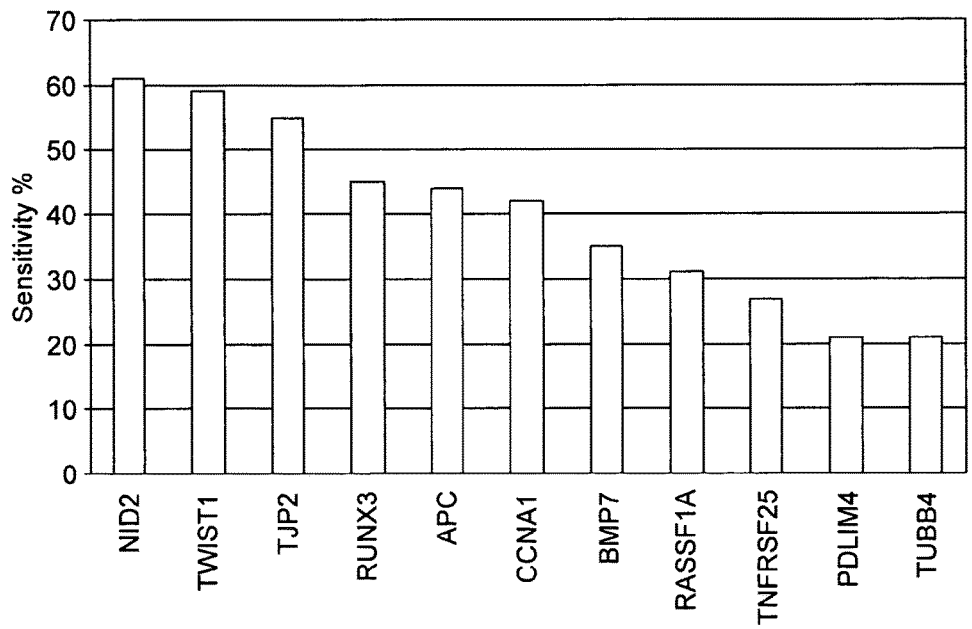
FIG. 3. Individual gene assay performance (% sensitivity) using the training set consisting of urine samples from 143 controls (non cancerous disease) and 62 patients with bladder carcinomas for real-time MSP.

Marker testing in urine samples: Eleven of the best performing markers in tissue were assessed on 218 available urine samples from standardized multicenter collections. These urine samples included 150 samples from patients without cancer and 68 samples from patients covering all stages of Bladder cancer. Testing yielded valid results from 143 controls and 62 bladder cancer cases. The individual performance (sensitivity and specificity) of the 11 gene assays is shown in FIG. 3 and the best panel is shown in Table 4. The case report forms of all patients were reviewed by a urologist. The 62 bladder cancer cases were classified into several cancer groups (4 papilloma, 17 Ta, 2 Tis, 14 T1, 14 T2, 2 T3 and 9 unknown) as shown in Table 4.

TABLE 4

Performance of one urine marker panel within different sample groups

| Sample groups | Urine panel: NID2, BMP7, TWIST1, CCNA1 and RUNX3 Sensitivity % (# positive/# total) [95% CI] |
|---|---|
| Papilloma | 75 (3/4) |
| Ta | 94 (16/17) |
| Tis | 100 (2/2) |
| T1 | 71 (10/14) |
| T2 | 100 (14/14) |
| T3 | 50 (1/2) |
| Unknown | 78 (7/9) |
| Early stages cancers (Papilloma, Ta, Tcis, T1 and T2) | 88% Sensitivity (45/51) [79-97] |
| All Cancer stages | 85% Sensitivity (53/62) [76-94] |
| Controls (symptomatic non-cancerous patients) | 93% Specificity (10/143) [89-97] |

The 143 controls (age matched) were classified into several control groups (57 Prostatitis, 5 benign prostatic hypertrophy [BPH], 12 high-grade prostatic intraepithelial neoplasia [HGPIN], 7 Urethral stricture, 7 Stones [bladder or kidney], 2 BOO [Bladder outlet obstruction], 7 LUTS [lower urinary tract symptoms, 2 Cystitis, 44 others). Methylation and Cytology results were compared when processing on the same urine samples (Table 5). The performance of the methylation tests among the different sample collection sites is presented in Table 6.

TABLE 5

Comparison of cytology and methylation results

|  |  | Cancer cases | Control cases | Sensitivity % (# positive/ # total) | Specificity % (# positive/ # total) |
|---|---|---|---|---|---|
| Cytology results | Negative | 31 | 43 | 38% (19/50) | 96% (2/45) |
|  | Positive/ Atypia | 19 | 2 |  |  |
| Methylation results | Negative | 9 | 133 | 85% (53/62) | 93% (10/143) |
|  | Positive | 53 | 10 |  |  |

TABLE 6

Performance of methylation tests among the different sample collection sites.

|  | Sensitivity % (# positive/# total) | Specificity % (# positive/# total) |
|---|---|---|
| Site 1 | 78% (18/23) | 92% (5/64) |
| Site 2 | 93% (14/15) | 95% (2/40) |
| Site 3 | 88% (21/24) | 92% (3/39) |

Example 2

A Real-time MSP Assay for Early Detection of Bladder Cancer—Urine Training Set 2

Figure 4:
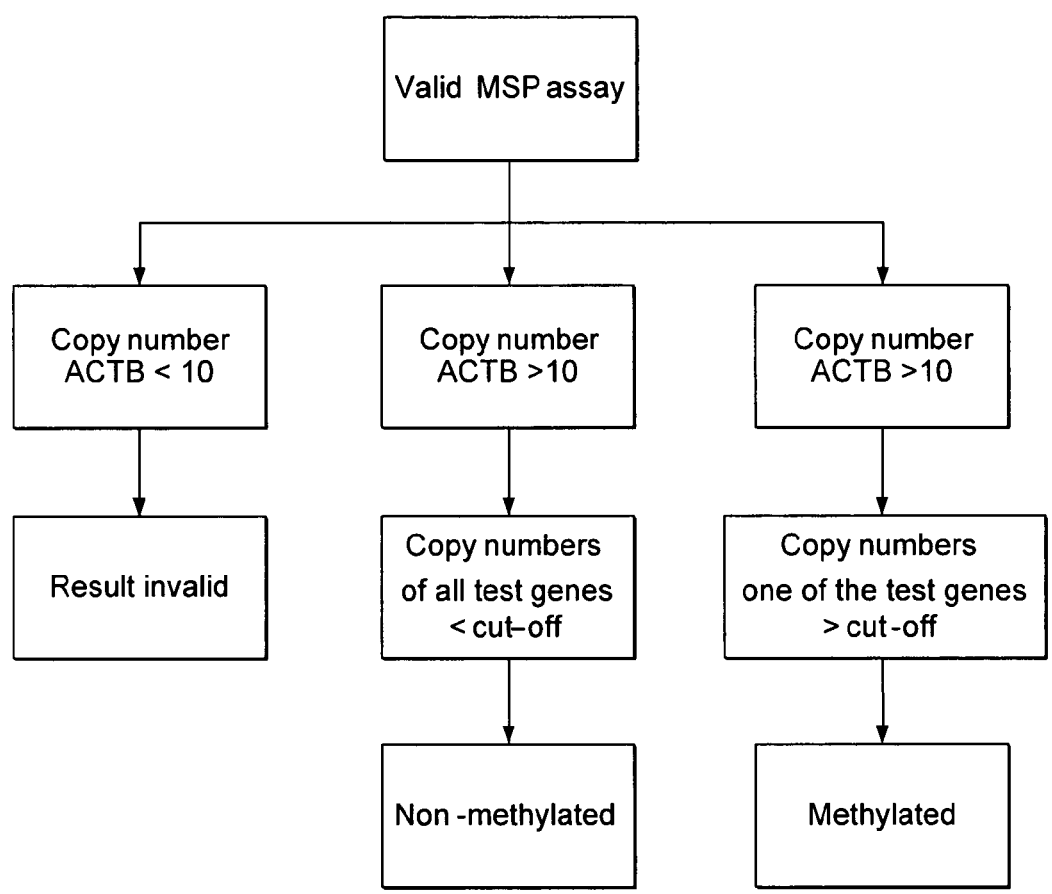
FIG. 4. Decision tree for sample classification (Methylated, Non-Methylated or Invalid) for urine training set 2 (Example 2) and 3 (Example 4).
Figure 5A:
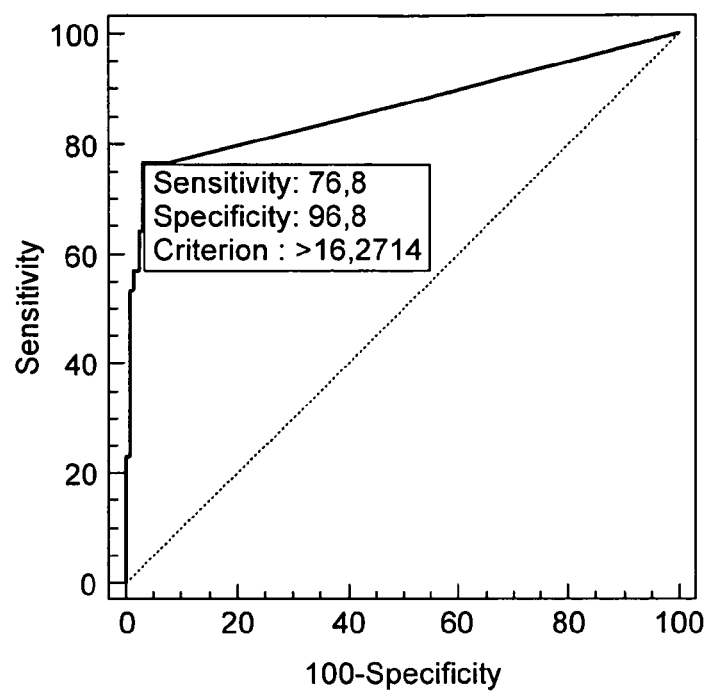
FIGS. 5A, 5B, 5C and 5D. Receiver Operating Characteristics (ROC) curves were calculated for TWIST1, RUNX3, NID2 and the three gene panel by plotting the true positive rate (sensitivity) against the false positive rate (100-specificity)
Figure 5B:
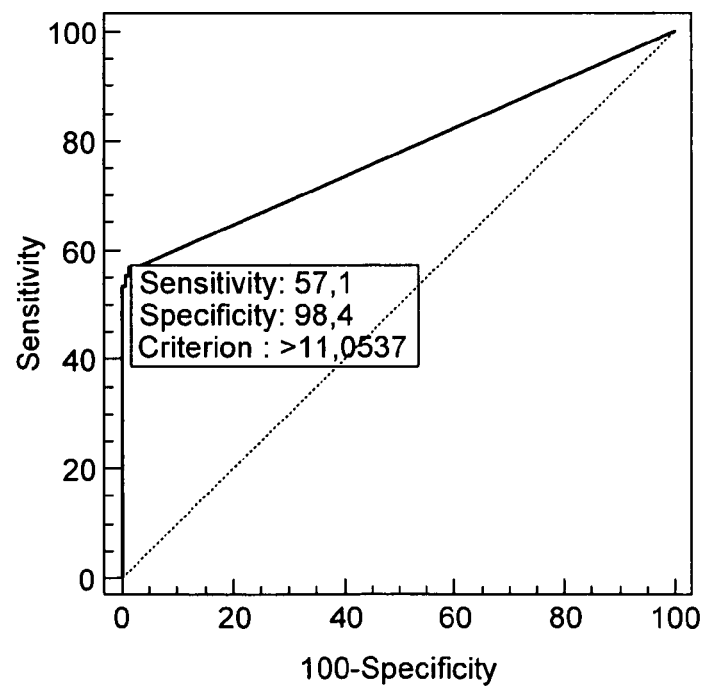
Figure 5C:
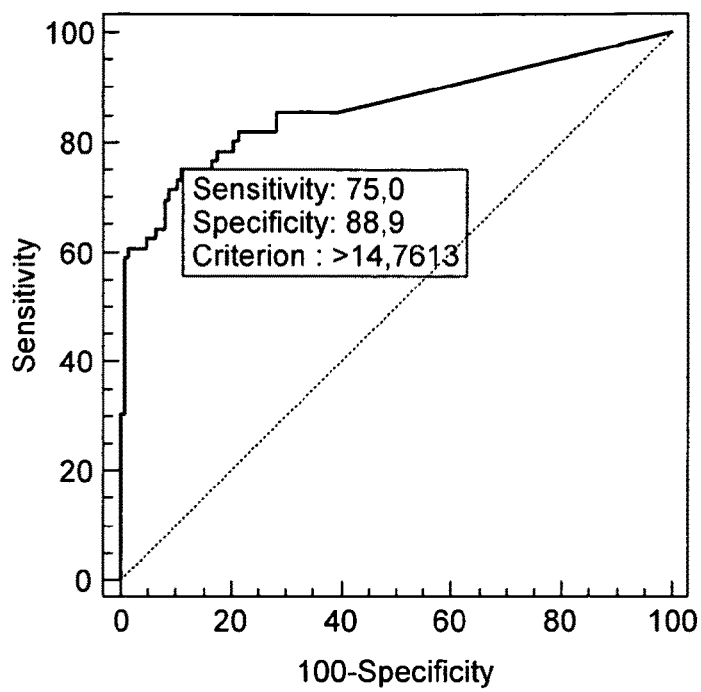
Figure 5D:
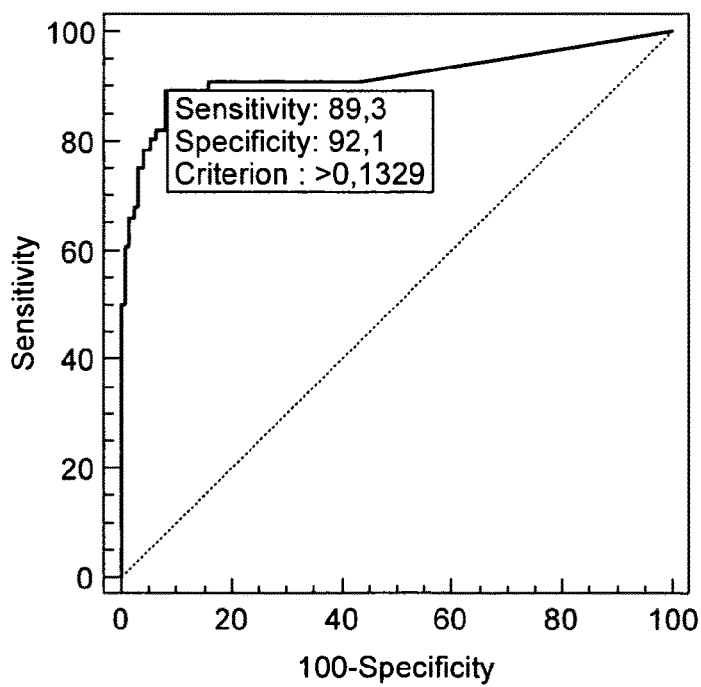

The 5-marker panel from Example 1 was further studied with an independent sample set, referred to as 'urine training set 2'. Due to a reduction of the number of genes tested (5 instead of 11), a greater aliquot of sample was available for each assay tested, resulting in an adapted BT elution volume and a different decision tree (based on copies rather than ratios) for analyzing the results (FIG. 4).

Materials and Methods

Marker identification: Candidate genes were identified using re-expression profiles of bladder cancerous cell lines, as discussed in Example 1.

Marker selection: Differentially methylated genes were validated in tissue using real-time methylation specific PCR (real-time MSP). Best performing tissue markers were selected for testing DNA from urine samples, as discussed in Example 1.

Urine sample collection: Prospective, randomly collected urine samples from multiple centers were used, as discussed in Example 1. All study participants received appropriate approval from the relevant ethical committee. Symptomatic patients (who had given their informed consent), attending a urology clinic and ultimately diagnosed with bladder cancer or other non-malignant urological disorders, provided a urine sample for use in real-time MSP and cytology analysis. From this ongoing trial, 415 urine samples were tested. Those included 285 samples from patients with no evidence of cancer and 130 samples from patients covering all stages of bladder cancer, with 88% representing early stage diseases.

Urine sample preparation: The collected urine sample was aliquoted in 50 ml portions for further processing. Each 50 ml aliquot was centrifuged within 4 h (of collection) at 3000 g for 10 min. The urine sediments were stored at −20° C. up to 6 months, as discussed in Example 1.

DNA preparation and processing: DNA was isolated from urine sediments using a standard method (i.e. Qiagen #158908 and Qiagen #158912) and quantified using the Picogreen® dsDNA quantitation kit (Molecular Probes, #P7589) following the manufacturer's directions. Up to 1.5 µg DNA was used for the bisulphite modification using a commercially available kit (i.e. Zymo, #D5002). This reaction selectively deaminates unmethylated cytosine residues resulting in a conversion to uracil, while 5-methyl cytosine residues are not modified. The modified DNA was eluted into 20 µl Tris-HCl (1 mM, pH 8.0) and then stored at −80° C. up to 6 months.

Real-time MSP: Analyte (TWIST, RUNX3, NID2, and ACTB) quantifications were performed by real-time MSP assays. These consisted of parallel amplification/quantification processes using specific primers and probes for each analyte and Molecular Beacon® assay formats on an ABI Prism® 7900HT instrument (Applied Biosystems). The analytes defined in the real-time MSP were the TWIST, RUNX3, and NID2 promoter sequences detecting the fully methylated versions. ACTB was used as a reference gene, using primers which were outside any CpG islands. The PCR reaction volume was 12.5 µl including 2.4 µl modified template DNA. Samples were classified as methylated, non-methylated, or invalid based on the decision tree shown in FIG. 4.

Amplicon sizes were as follows:
TWIST1: 77 bp
RUNX3: 127 bp
NID2: 99 bp
ACTB: 103 bp
Sequence details were as follows:

```
Forward Primer TWIST1:
                                         (SEQ ID NO: 22)
5' - GTTAGGGTTCGGGGGCGTTGTT - 3'

Reverse Primer TWIST1:
                                         (SEQ ID NO: 23)
5' - CCGTCGCCTTCCTCCGACGAA - 3'

Forward Primer RUNX3:
                                         (SEQ ID NO: 31)
5' - CGTAGGGTTGTATTTGAGCGA - 3'

Reverse Primer RUNX3:
                                         (SEQ ID NO: 32)
5' - TAACTTTTAACGAAATTACCCCG - 3'

Forward Primer NID2:
                                         (SEQ ID NO: 40)
5' - GCGGTTTTTAAGGAGTTTTATTTTC - 3'

Reverse Primer NID2:
                                         (SEQ ID NO: 41)
5' - CTACGAAATTCCCTTTACGCT - 3'

Forward Primer ACTB:
                                         (SEQ ID NO: 46)
5' - TAGGGAGTATATAGGTTGGGGAAGTT -3'
```

-continued

Reverse Primer ACTB:
(SEQ ID NO: 47)
5' - AACACACAATAACAAACACAAATTCAC - 3'

Molecular Beacon TWIST1:
(SEQ ID NO: 24)
5' - Fam-CGACATGCCGGCGGGGAAGGAAATCGTTTCGCATGTCG-
Dabcyl - 3'

Molecular Beacon RUNX3:
(SEQ ID NO: 33)
5' - Fam-CGACATGCCGGGTTAGGGGGCGTAAAATTTTATTCGTTGC
ATGTCG-Dabcyl - 3'

Molecular Beacon NID2:
(SEQ ID NO: 42)
5' - Fam-CGACATGGGTTCGTAAGGTTTCGGGTAGCGGCCATGTCG-
Dabcyl - 3'

Molecular Beacon ACTB:
(SEQ ID NO: 48)
5' - Fam-CGACTGCGTGTGGGGTGGTGATGGAGGAGGTTTAGGCAGTC
G-Dabcyl-3'

Target sequences are located as follows (all based on version 36.3 of the NCBI human genome):

TWIST1: chromosome 7, between positions 19124120 and 19124043 (RefSeq: NM_000474)

RUNX3: chromosome 1, between positions 25128341 and 25128468 (RefSeq: NM_004350)

NID2: chromosome 14, between positions 51605816 and 51605915 (RefSeq: NM_007361)

ACTB: chromosome 7, between positions 5538428 and 5538326 (RefSeq: NM_001101)

Thermal profile: The following was used for all genes: 95° C. for 5 min, 95° C. for 30 sec, 57° C. for 30 sec, and 72° C. for 30 sec for 45 cycles. The total PCR volume was 12.5 µl (including 2.4 µl DNA template) in a 384-well PCR plate.

Quantification: The results were generated using the SDS 2.2 software (Applied Biosystems), exported as Ct values (cycle number at which the amplification curves cross the threshold value, set automatically by the software), and then used to calculate copy numbers based on a linear regression of the values plotted on a standard curve of 20–2×10^6 gene copy equivalents, using plasmid DNA containing the bisulphite modified sequence of interest. Cell lines were included in each run as positive and negative controls, and entered the procedure at the DNA extraction step. A run was considered valid when the following five criteria were met: a) slopes of both standard curves above −4 (PCR efficiency >77.8*); b) r^2 of at least 4 relevant data points above 0.990; c) routinely included NTC not amplified; d) 10% of a 1 µg conversion reaction of the positive cell line assay control was detectable; and e) 10% of a 1 µg conversion reaction of the negative cell line assay control was not detected within the standard curve.

Results:

Assay validity rate in tissue and urine: One hundred and thirty formalin-fixed paraffin-embedded (FFPE) tissue samples and 415 urine samples were processed using real-time MSP (Table 7). The real-time MSP assays produced valid results in 96% of the FFPE samples and in 93% of the urine samples.

TABLE 7

Summary of samples evaluated by real-time MSP

| Sample sets | Sample types | Sample numbers | Valid tests [%] |
| --- | --- | --- | --- |
| Tissue training set | Cancer | 53 | 53/53 [100] |
|  | Controls | 30 | 25/30 [83] |
|  | Total | 83 | 78/83 [94] |
| Tissue test set | Cancer | 38 | 38/38 [100] |
|  | Controls | 9 | 9/9 [100] |
|  | Total | 47 | 47/47 [100] |
| Tissue sets combined | Cancer | 91 | 91/91 [100] |
|  | Controls | 39 | 34/39 [87] |
|  | Total | 130 | 125/130 [96] |
| Urine training set 1 | Cancer | 68 | 62/68 [91] |
|  | Controls | 150 | 143/150 [95] |
|  | Total | 218 | 205/218 [94] |
| Urine training set 2 | Cancer | 62 | 56/62 [90] |
|  | Controls | 135 | 126/135 [93] |
|  | Total | 197 | 182/197 [92] |
| Urine sets combined | Cancer | 130 | 118/130 [91] |
|  | Controls | 285 | 269/285 [94] |
|  | Total | 415 | 387/415 [93] |

Marker selection in bladder tissue: Results are discussed in Example 1, with reference to FIG. 2 and table 3.

Marker testing in urine samples: Eleven of the best performing markers in tissue were assessed on 218 available urine samples from standardized multicenter collections (urine training set 1). These results are discussed in Example 1 and are repeated in table 8 below.

The case report forms of the 218 patients from the first training set (Example 1) were reviewed by an urologist. The 62 bladder cancer cases were classified into several cancer groups (4 papilloma, 17 Ta, 2 Tis, 14 T1, 14 T2, 2 T3 and 9 unknown). The 143 controls (age matched) were classified into several control groups (60 prostatitis, 8 BPH [benign prostatic hypertrophy], 12 HGPIN [high-grade prostatic intraepithelial neoplasia], 7 urethral stricture, 8 stones [bladder or kidney], 2 BOO [bladder outlet obstruction], 7 LUTS [lower urinary tract symptoms], 3 cystitis, 6 incontinency, 4 prolapsus, 2 hydronephrosis, 2 orchitis, 4 others).

The best performing marker panel in the first urine training set (5 genes, Example 1) was further studied with an independent sample set prospectively collected from the ongoing trial (urine training set 2). The further reduction in the numbers of tested genes, resulting in fewer assays per sample, allowed a greater aliquot of sample in each assay. The urine samples in the second training set included 135 samples from patients without cancer and 62 samples from patients covering the early stages of bladder cancer. Testing yielded valid results from 126 controls and 56 bladder cancer cases (Table 7). The case report forms of those 182 patients were reviewed by an urologist. The 56 bladder cancer cases were classified into several cancer groups (6 papilloma, 19 Ta, 4 Tis, 12 T1, 12 T2, and 3 unknown). The 126 controls (age matched) were classified into several control groups (19 prostatitis, 30 BPH [benign prostatic hyperplasia], 18 incontinency, 14 lithiasis, 6 urethral stricture, 2 BOO [bladder outlet obstruction], 3 LUTS [lower urinary tract symptoms], 9 cystitis, 5 urinary infection, 4 vesical instability, 5 prolapsus, 11 others). A panel of 3 urine-based methylation markers demonstrated 91% sensitivity and 93% specificity in identifying patients with early stage bladder cancer (Table 8). A logistic regression model was also build using the three markers. The Receiver Operating Characteristics (ROC) curve for this logistic regression model was calculated for the bladder gene panel by plotting the true positive rate (sensitivity) in function of the false positive rate (100-specificity). The area under the curve (AUC) is 0.919. The 95% CI range was 0.870 to 0.995 at a significance of P=0.0001 for area=5 (FIG. 5). The optimal sensitivity and specificity obtained with this model were similar to the ones obtained with the simple linear interpretation models (if any marker gives a copy number above the cutoff, the sample is scored as positive) used for tables 8 to 10.

TABLE 8

Performance of urine marker panels within different sample groups. Copy cutoffs used for training set 2 were: TWIST1 = 17, RUNX3 = 5 and NID2 = 30.

| Sample groups | Training set 1 (Example 1, table 4) NID2, BMP7, TWIST1, CCNA1 and RUNX3 Sensitivity % (# positive/# total) [95% CI] | Training set 2 TWIST, RUNX3, NID2 Sensitivity % (# positive/# total) [95% CI] |
|---|---|---|
| Papilloma | 75 (3/4) | 100 (6/6) |
| Ta | 94 (16/17) | 84 (16/19) |
| Tis | 100 (2/2) | 100 (4/4) |
| T1 | 71 (10/14) | 100 (12/12) |
| T2 | 100 (14/14) | 83 (10/12) |
| T3 | 50 (1/2) | / |
| Unknown | 78 (7/9) | 100 (3/3) |
| Early cancer stages (Papilloma, Ta, Tis, T1 and T2) | 88% Sensitivity (45/51) [79-97] | 91% Sensitivity (48/53) [80-97] |
| All cancer stages | 85% Sensitivity (53/62) [77-94] | 91% Sensitivity (51/56) [80-97] |
| Controls (symptomatic non-cancerous patients) | 93% Specificity (10/143) [89-97] | 93% Specificity (9/126) [87-97] |

Methylation and cytology results (both urine training sets) were compared on the same urine samples (Table 9).

TABLE 9

Comparison of currently available cytology results with methylation

| Results | | Cancer cases | Control cases | Sensitivity % (# positive/# total) [95% CI] | Specificity % (# positive/# total) [95% CI] |
|---|---|---|---|---|---|
| Training set 1 | | | | | |
| Cytology results | Negative | 39 | 132 | 37% (23/62) [25-49] | 96% (6/138) [92-99] |
| | Positive/Atypia | 23 | 6 | | |
| Methylation results | Negative | 9 | 133 | 85% (53/62) [77-94] | 93% (10/143) [89-97] |
| | Positive | 53 | 10 | | |
| Training set 2 | | | | | |
| Cytology results | Negative | 32 | 119 | 43% (24/56) [30-56] | 94% (7/126) [90-98] |
| | Positive/Atypia | 24 | 7 | | |
| Methylation results | Negative | 5 | 117 | 91% (51/56) [84-99] | 93% (9/126) [90-98] |
| | Positive | 51 | 9 | | |

The sensitivity of the 3-marker methylation panel was significantly higher than the sensitivity of cytology (91% versus 43%) while the specificity was similar (93% versus 94%).

The performance of the methylation tests among the different sample collection sites was highly reproducible (Table 10).

TABLE 10

Performance of valid methylation tests among the different sample collection sites.

| Sample collection sites | Sample sets | Sensitivity % (# positive/# total) | Specificity % (# positive/# total) |
|---|---|---|---|
| Site 1 | training set 1 | 78% (18/23) | 92% (5/64) |
| | training set 2 | 89% (8/9) | 91% (2/21) |
| Site 2 | training set 1 | 93% (14/15) | 95% (2/40) |
| | training set 2 | 93% (28/30) | 94% (3/52) |
| Site 3 | training set 1 | 88% (21/24) | 92% (3/39) |
| | training set 2 | 88% (15/17) | 93% (4/53) |

Example 3

Non-invasive Combined Approach

To further enhance the sensitivity of the new urine-based DNA methylation assay, the inventors investigated the feasibility of combining their methylation test with established methods for the detection of early-stage bladder cancer in urine samples. Conventional urinary cytology (current standard-of-care procedure) and FGFR3 mutation analysis results (particularly useful for recurrence detection) were used to complement the methods of the invention.

Materials and Methods

Sample collection: samples from urine training set 1 and training set 2, as described in Examples 1 and 2, were used to demonstrate the utility of combining the methylation assay with cytology and/or FGFR3 mutation results.

Different Assays Tested:

OMS urine-based DNA methylation assay: Analyte (TWIST, RUNX3, NID2, and ACTB) quantifications were performed by real-time MSP assays as detailed above.

Urinary cytology: General procedure for cytology examination was applied (see McKee G. in: Gray W and McKee G T eds. Diagnostic Cytopathology. 2nd ed. Churchill Livingstone 2003)

High-throughput FGFR3 mutation analysis: Urine samples were processed through the snapshot assay as previously described in van Oers et al. With this method the analysis of 3 regions of the FGFR3 gene, located in exons 7, 10 and 15, are combined in one assay, allowing a sample to be screened for all FGFR3 mutations simultaneously. These regions comprise 9 potential codon mutations: R248C and S249C (exon 7), G372C, Y375C, and A393E (exon 10), and K652E, K652Q, K652M, and K652T (exon 15).

Results

Combining Methylation and Cytology Results:

Methylation and cytology results (from both urine training sets) were compared on the same urine samples (see Table 11).

Urine Training Set 1:

The sensitivity of the methylation panel was significantly higher than the sensitivity of cytology (85% versus 37%) while the specificity was rather similar (93% versus 97%).

The combination of methylation and cytology resulted in a Negative Predictive Value of >95% based on a bladder cancer prevalence of 31% in this high-risk population. (Negative predictive value (NPV) means the percentage of negative tests that are truly negative).

This combination resulted in a negative likelihood ratio (NLR) of 0.11 and a positive likelihood ratio (PLR) of 8.1 indicating the utility of such a combination of assays in assessing a high risk population for bladder cancer.

Urine Training Set 2:

The sensitivity of the methylation panel (3 preferred marker panel) was significantly higher than the sensitivity of cytology (91% versus 43%) while the specificity was similar (93% versus 94%).

The combination of methylation and cytology resulted in a Negative Predictive Value of >98% based on a bladder cancer prevalence of 31% in this high-risk population. This combination resulted in a NLR of 0.041 and a PLR of 8.1 indicating the utility of such a combination of assays in assessing a high risk population for bladder cancer.

NLR is a measure of the accuracy of a negative result and is calculated by the formula (1-Sensitivity)/Specificity. A PLR is a measure of the accuracy of a positive result and is calculated by the formula Sensitivity/(1-Specificity). (for example, a NLR of 0.04 means that one is 25 times (1/0.04) more likely to be truly negative with a negative test result and a PLR of 8 means you are 8 times more likely to be truly positive with a positive test)

Combining methylation, cytology and FGFR3 mutation results: Methylation, cytology and FGFR3 mutation results were compared on the same urine samples (Table 12). In total, 61 samples were randomly selected from both urine training sets (41 cancer cases and 20 control samples) and processed through the 3 separate methods using primers and reaction conditions as indicated above.

TABLE 12

Sample group classification of samples tested through methylation, cytology and FGFR3 mutation test

| Sample groups | 61 tested urine samples |
| --- | --- |
| Papilloma | 4 |
| Ta | 13 |
| Tis | 3 |
| T1 | 8 |
| T2 | 6 |
| T3 | 1 |
| Unknown | 6 |
| Controls (symptomatic non-cancerous patients) | 20 |

The results obtained are summarized below in Table 13. A combined result is considered negative when a negative signal (0, NEG, WT) was obtained for all 3 assays, alternatively a combined result is considered positive when at least one method was positive (1, ATYPIA or MT).

TABLE 11

Combined results cytology-methylation using same sample set

| | Urine training set 1 | | | Urine training set 2 | | |
| --- | --- | --- | --- | --- | --- | --- |
| | Methylation Results | Cytology Results | Combination | Methylation Results | Cytology Results | Combination |
| Total cancer | 62 | 62 | 62 | 56 | 56 | 56 |
| POS | 53 | 23 | 56 | 51 | 24 | 54 |
| NEG | 9 | 39 | 6 | 5 | 32 | 2 |
| Sensitivity | 85% | 37% | 90% | 91% | 43% | 96% |
| Total controls | 143 | 138 | 143 | 126 | 126 | 126 |
| POS | 10 | 6 | 16 | 9 | 7 | 15 |
| NEG | 133 | 132 | 127 | 117 | 119 | 111 |
| Specificity | 93% | 97% | 89% | 93% | 94% | 88% |

TABLE 13

Combined results methylation, cytology and FGFR3 mutation using same sample set

| Patient No | Methylation Results | Cytology Results | FGFR3 mutation | Combination Methylation/ Cytology | Combination Methylation/ FGFR3 | Combination Cytology/ FGFR3 | Combination Methylation/ Cytology/ FGFR3 |
|---|---|---|---|---|---|---|---|
| Case 1 | 1 | ATYPIA | MT | POS | POS | POS | POS |
| Case 2 | 1 | NEG | WT | POS | POS | NEG | POS |
| Case 3 | 1 | NEG | MT | POS | POS | POS | POS |
| Case 4 | 1 | NEG | WT | POS | POS | NEG | POS |
| Case 5 | 1 | ATYPIA | MT | POS | POS | POS | POS |
| Case 6 | 1 | POS | WT | POS | POS | POS | POS |
| Case 7 | 1 | NEG | WT | POS | POS | NEG | POS |
| Case 8 | 1 | POS | MT | POS | POS | POS | POS |
| Case 9 | 1 | POS | MT | POS | POS | POS | POS |
| Case 10 | 1 | NEG | WT | POS | POS | NEG | POS |
| Case 11 | 0 | NEG | WT | NEG | NEG | NEG | NEG |
| Case 12 | 1 | NEG | MT | POS | POS | POS | POS |
| Case 13 | 1 | POS | MT | POS | POS | POS | POS |
| Case 14 | 1 | POS | MT | POS | POS | POS | POS |
| Case 15 | 1 | NEG | WT | POS | POS | NEG | POS |
| Case 16 | 1 | NEG | MT | POS | POS | POS | POS |
| Case 17 | 1 | NEG | MT | POS | POS | POS | POS |
| Case 18 | 1 | POS | MT | POS | POS | POS | POS |
| Case 19 | 1 | NEG | MT | POS | POS | POS | POS |
| Case 20 | 1 | NEG | WT | POS | POS | NEG | POS |
| Case 21 | 0 | ATYPIA | MT | POS | POS | POS | POS |
| Case 22 | 0 | NEG | MT | NEG | POS | POS | POS |
| Case 23 | 1 | NEG | WT | POS | POS | NEG | POS |
| Case 24 | 1 | ATYPIA | WT | POS | POS | POS | POS |
| Case 25 | 1 | NEG | MT | POS | POS | POS | POS |
| Case 26 | 0 | ATYPIA | WT | POS | NEG | POS | POS |
| Case 27 | 1 | NEG | WT | POS | POS | NEG | POS |
| Case 28 | 1 | NEG | WT | POS | POS | NEG | POS |
| Case 29 | 1 | NEG | MT | POS | POS | POS | POS |
| Case 30 | 1 | NEG | WT | POS | POS | NEG | POS |
| Case 31 | 1 | POS | WT | POS | POS | POS | POS |
| Case 32 | 1 | POS | WT | POS | POS | POS | POS |
| Case 33 | 0 | NEG | WT | NEG | NEG | NEG | NEG |
| Case 34 | 1 | ATYPIA | MT | POS | POS | POS | POS |
| Case 35 | 1 | NEG | WT | POS | POS | NEG | POS |
| Case 36 | 1 | POS | WT | POS | POS | POS | POS |
| Case 37 | 1 | ATYPIA | WT | POS | POS | POS | POS |
| Case 38 | 1 | POS | WT | POS | POS | POS | POS |
| Case 39 | 1 | NEG | WT | POS | POS | NEG | POS |
| Case 40 | 1 | NEG | WT | POS | POS | NEG | POS |
| Case 41 | 1 | NEG | WT | POS | POS | NEG | POS |
| Total Cancers | 41 | 41 | 41 | 41 | 41 | 41 | 41 |
| POS | 36 | 17 | 17 | 38 | 38 | 25 | 39 |
| NEG | 5 | 24 | 24 | 3 | 3 | 16 | 2 |
| Sensitivity | 88% | 42% | 42% | 93% | 93% | 61% | 95% |
| Control 1 | 0 | NEG | WT | NEG | NEG | NEG | NEG |
| Control 2 | 0 | NEG | WT | NEG | NEG | NEG | NEG |
| Control 3 | 0 | NEG | WT | NEG | NEG | NEG | NEG |
| Control 4 | 0 | NEG | WT | NEG | NEG | NEG | NEG |
| Control 5 | 0 | NEG | WT | NEG | NEG | NEG | NEG |
| Control 6 | 0 | NEG | WT | NEG | NEG | NEG | NEG |
| Control 7 | 0 | NEG | WT | NEG | NEG | NEG | NEG |
| Control 8 | 0 | NEG | WT | NEG | NEG | NEG | NEG |
| Control 9 | 0 | NEG | WT | NEG | NEG | NEG | NEG |
| Control 10 | 0 | NEG | WT | NEG | NEG | NEG | NEG |
| Control 11 | 1 | ATYPIA | WT | POS | POS | POS | POS |
| Control 12 | 0 | NEG | WT | NEG | NEG | NEG | NEG |
| Control 13 | 0 | NEG | WT | NEG | NEG | NEG | NEG |
| Control 14 | 0 | NEG | WT | NEG | NEG | NEG | NEG |
| Control 15 | 0 | NEG | WT | NEG | NEG | NEG | NEG |
| Control 16 | 0 | NEG | WT | NEG | NEG | NEG | NEG |
| Control 17 | 0 | NEG | WT | NEG | NEG | NEG | NEG |
| Control 18 | 0 | NEG | WT | NEG | NEG | NEG | NEG |
| Control 19 | 0 | NEG | WT | NEG | NEG | NEG | NEG |
| Control 20 | 0 | NEG | WT | NEG | NEG | NEG | NEG |
| Total controls | 20 | 20 | 20 | 20 | 20 | 20 | 20 |

TABLE 13-continued

Combined results methylation, cytology and FGFR3 mutation using same sample set

| Patient No | Methylation Results | Cytology Results | FGFR3 mutation | Combination Methylation/ Cytology | Combination Methylation/ FGFR3 | Combination Cytology/ FGFR3 | Combination Methylation/ Cytology/ FGFR3 |
|---|---|---|---|---|---|---|---|
| POS | 1 | 1 | 0 | 1 | 1 | 1 | 1 |
| NEG | 19 | 19 | 20 | 19 | 19 | 19 | 19 |
| Specificity | 95% | 95% | 100% | 95% | 95% | 95% | 95% |
| PLR | 4.67 | 1.69 | 1.83 | 7.15 | 7.15 | 2.10 | 10.24 |
| NLR | 0.03 | 0.13 | 0 | 0.03 | 0.03 | 0.07 | 0.03 |

(1 = Methylated, 0 = Unmethylated, MT = Mutant, WT = Wild type, POS = Positive, NEG = Negative, ATYPIA = Atypical suspiscious cells)

The results clearly show that conventional urinary cytology and FGFR3 mutation analysis can be used to complement the methylation assay. Combining the outcome of these 3 assays resulted in a NLR of 0.03 and a PLR of 10.24 indicating that such combination of assays would be very useful in the clinic to aid the urologist in determining whether a patient had bladder cancer or not.

The reported short-coming of all currently available tests is the poor specificity. The combination of different methods for bladder cancer detection has been shown to improve sensitivity but at the expensive of its specificity. Our non-invasive combined approach yielded a sensitivity of 95% while maintaining the high specificity values (95%) of our methylation test. These results underline the predictive potential of combining urinary cytology (regarded as standard-of-care procedure) with our methylation test. These results clearly show that this non-invasive combined approach offers a valuable alternative for the urine-based marker tests currently available.

Example 4

A Real-time MSP Assay for Early Detection of Bladder Cancer—Urine Training Set 3

Typically urine samples are centrifuged within 4 hours of collection in order to avoid DNA degradation. The inventors have shown (see International Application PCT/GB2008/002093) that adding stabilizing buffer to the urine sample avoids the need for centrifugation shortly after urine collection. Samples can be kept at room temperature for up to 72 hours following addition of a stabilizing buffer, without requirement for centrifugation, while maintaining the DNA-integrity.

The 3-marker panel from Example 2 was tested on an independent sample set, referred to as 'urine training set 3'. In this training set, freshly collected urine samples were stored with stabilizing buffer for up to 72 h at room temperature before centrifugation.

Materials and Methods

Material and methods are identical to what is described above in example 2, except for the urine sample preparation. Instead of centrifuging the urine sample within 4 h at 3000 g for 10 min, stabilizer (Stabilur® tablets, Cargille Laboratories, #40050, 5 tablets per 50 ml urine) was added to the urine at the time of collection. The urine sample was then held at room temperature up to 72 h before centrifugation. The urine sediments were stored at −20° C. up to 6 months and further processed as discussed in example 2.

Results:

Assay validity rate in tissue and urine: One hundred and thirty formalin-fixed paraffin-embedded (FFPE) tissue samples and 495 urine samples were processed using real-time MSP (Table 14). The real-time MSP assays produced valid results in 96% of the FFPE samples and in 94% of the urine samples.

TABLE 14

Summary of samples evaluated by real-time MSP

| Sample sets | Sample types | Sample numbers | Valid tests [%] |
|---|---|---|---|
| Tissue training set | Cancer | 53 | 53/53 [100] |
| | Controls | 30 | 25/30 [83] |
| | Total | 83 | 78/83 [94] |
| Tissue test set | Cancer | 38 | 38/38 [100] |
| | Controls | 9 | 9/9 [100] |
| | Total | 47 | 47/47 [100] |
| Tissue sets combined | Cancer | 91 | 91/91 [100] |
| | Controls | 39 | 34/39 [87] |
| | Total | 130 | 125/130 [96] |
| Urine training set 1 | Cancer | 68 | 62/68 [91] |
| | Controls | 150 | 143/150 [95] |
| | Total | 218 | 205/218 [94] |
| Urine training set 2 | Cancer | 62 | 56/62 [90] |
| | Controls | 135 | 126/135 [93] |
| | Total | 197 | 182/197 [92] |
| Urine training set 3 | Cancer | 32 | 32/32 [100] |
| | Controls | 48 | 45/48 [94] |
| | Total | 80 | 77/80 [96] |
| Urine sets combined | Cancer | 162 | 150/162 [93] |
| | Controls | 333 | 314/333 [94] |
| | Total | 495 | 464/495 [94] |

Marker selection in bladder tissue: Results are discussed in Example 1, with reference to FIG. 2 and table 3.

Marker testing in urine samples: The best performing marker panel in the first urine training set (5 genes, Example 1) was further studied with an independent sample set prospectively collected from the ongoing trial (urine training set 2). The further reduction in the numbers of tested genes, resulting in fewer assays per sample, allowed a greater aliquot of sample in each assay. These results are discussed in Example 2 and are repeated in table 15 below.

Urine samples from the third training set included 48 samples from patients without cancer and 32 samples from patients covering the early stages of bladder cancer. Testing yielded valid results from 45 controls and 32 bladder cancer cases (Table 14). The case report forms of those 80 patients were reviewed by an urologist. The 32 bladder cancer cases were classified into several cancer groups (2 papilloma, 13

Ta, 1 Tis, 9 T1, 5 T2, 1 epidermoid carcinoma and 1 unknown). The 45 controls (age matched) were classified into several control groups (21 prostatitis, 3 BPH [benign prostatic hyperplasia], 2 hydrocoel, 1 Epididymite, 1 urethral stricture, 1 LUTS [lower urinary tract symptoms], 1 vesical instability, 1 prolapsus, 14 unknown).

Samples were classified as methylated, non-methylated, or invalid based on the decision tree shown in FIG. 4. In this linear interpretation model a sample is scored positive if any marker gives a copy number above the cutoff. Cutoffs were adapted for both training sets to obtain optimal sensitivity and specificity results and are shown in Table 15. Cutoff of the reference gene ACTB was set at 15 copies.

TABLE 15

Performance of one urine marker panel within different sample groups. Applied cutoffs are noted between brackets adjacent to the marker name.

| Sample groups | Training set 2<br>TWIST1 (7.5), RUNX3 (5) and NID2 (30)<br>Sensitivity %<br>(# positive/# total)<br>[95% CI] | Training set 3<br>TWIST1 (7.5), RUNX3 (5) and NID2 (30)<br>Sensitivity %<br>(# positive/# total)<br>[95% CI] |
|---|---|---|
| Papilloma | 100 (6/6) | 50 (1/2) |
| Ta | 84 (16/19) | 85 (11/13) |
| Tis | 100 (4/4) | 100 (1/1) |
| T1 | 100 (12/12) | 100 (9/9) |
| T2 | 83 (10/12) | 100 (5/5) |
| Epidermoid carcinoma | / | 100 (1/1) |
| Unknown | 100 (3/3) | 100 (1/1) |
| All cancer stages | 91% Sensitivity (51/56) [80-97] | 91% Sensitivity (29/32) [81-100] |
| Controls (symptomatic) | 91% Specificity (11/124) [86-96] | 91% Specificity (4/45) [82-99] |

Comparable results were obtained for training set 2 and training set 3 independent of whether urine samples were centrifuged within 4 h of collection or stabilized upon collection and held at room temperature for up to 72 h before centrifugation.

The third study, performed on an independent sample set confirmed that the urine based methylation assay (TWIST1, RUNX3 and NID2) correctly identified 91% of all tested bladder cancers at a false positive rate of only 9% (91% specificity).

The individual performance of the TWIST1 gene in urine training set 2 and 3 is shown in Table 16.

A specificity of 95% was obtained with a corresponding sensitivity of 77% and 91% respectively.

TABLE 16

Twist1 individual gene assay performance displaying % specificity and % sensitivity for urine training sets 2 and 3 (applied cutoff for TWIST1 = 7.5, for ACTB = 15)

| Sample groups | Training set 2<br>TWIST1 (7.5)<br>Sensitivity %<br>(# positive/# total)<br>[95% CI] | Training set 3<br>TWIST1 (7.5)<br>Sensitivity %<br>(# positive/# total)<br>[95% CI] |
|---|---|---|
| Papilloma | 83 (5/6) | 50 (1/2) |
| Ta | 74 (14/19) | 85 (11/13) |
| Tis | 75 (3/4) | 100 (1/1) |
| T1 | 75 (9/12) | 100 (9/9) |
| T2 | 75 (9/12) | 100 (5/5) |
| Epidermoid carcinoma | / | 100 (1/1) |

TABLE 16-continued

Twist1 individual gene assay performance displaying % specificity and % sensitivity for urine training sets 2 and 3 (applied cutoff for TWIST1 = 7.5, for ACTB = 15)

| Sample groups | Training set 2<br>TWIST1 (7.5)<br>Sensitivity %<br>(# positive/# total)<br>[95% CI] | Training set 3<br>TWIST1 (7.5)<br>Sensitivity %<br>(# positive/# total)<br>[95% CI] |
|---|---|---|
| Unknown | 100 (3/3) | 100 (1/1) |
| All cancer stages | 77% Sensitivity (43/56) [66-88] | 91% Sensitivity (29/32) [81-100] |
| Controls (symptomatic) | 95% Specificity (6/124) [91-99] | 95% Specificity (2/44) [89-102] |

REFERENCES

Akey D T, Akey J M, Zhang K, Jin L. Assaying DNA methylation. based on high-throughput melting curve approaches. Genomnics. 2002 October; 80(4):376-84.

Barringer K J, Orgel. L, Wahl G, Gingeras T R. Blunt-end and single-strand ligations by *Escherichia coli* ligase: influence on an in vitro amplification scheme. Gene. 1990 Apr. 30; 89(1):117-22.

Conmpton J. Nucleic acid sequence-based amplification. Nature. 1991 Mar. 7; 350(6313):91-2.

Cottrell S E, Distler J, Goodman N S, Mooney S H, Kluth A, Olek A, Schwope I, Tetzner R, Ziebarth H, Berlin K. A real-time PCP assay for DNA-methylation using methylation-specific blockers. Nucleic Acids Res. 2004 Jan. 13; 32(1):e10

Di Vinci A, Gelvi I, Banelli B, Casciano I, Allemanni G, Romani M; Meth-DOP-PCR: an assay for the methylation profiling of trace amounts of DNA extracted from bodily fluids; Lab invest. 2006 March; 86(3):297-303;

Eads C A, Danenberg K D, Kawakami K, Saltz L B, Blake C, Shibata D, Danenberg P V, Laird P W. MethyLight: a high-throughput assay to measure DNA methylation. Nucleic Acids Res. 2000 Apr. 15; 28(8):E32.

Esteller M, Corn P G, Baylin S B, Herman J G. A gene hypermethylation profile of human cancer. Cancer Res 2001; 61:3225-9.

Fahy E, Kwoh D Y, Gingeras T R. Self-sustained sequence replication (3SR): an isothermal transcription-based amplification system alternative to PCR. PCR Methods Appl. 1991 August; 1(1):25-33. Review Herman J G, Graff J R, Myöhänen S, Nelkin B D, Baylin S B. Methylation-specific PCR: a novel PCR assay for methylation status of CpG islands. Proc Natl Acad Sci USA. 1996 Sep. 3; 93(18):9821-6

Furuichi Y, Wataya Y, Hayatsu H, Ukita T. Chemical modification of tRNA-Tyr-yeast with hisulphite. A new method to modify isopentenyladenosine residue. hem Biophys Res Commun. 1970 Dec. 9; 41(5):1185-91

Jones P. A. and Baylin S. B. The fundamental role of epigenetic events in cancer. Nat Rev Genet 3 (2002), 415-428.

Melnikov A A, Gartenhaus R B, Levenson A S, Motchoulskaia N A, Levenson Chernokhvostov V V. MSRE-PCR for analysis of gene-specific DNA methylation. Nucleic Acids Res. 2005 Jun. 8; 33(10):e93.

Rand K, Qu W, Ho T, Clark S J, Molloy P. Conversion-specific detection of DNA methylation using real-time polymerase chain reaction (ConLight-MSP) to avoid false positives. Methods. 2002 June; 27(2):114-20.

Sasaki M, Anast J, Bassett W, Kawakami T, Sakuragi N, Dahiya P. Bisulphite conversion-specific and methylation-specific PCR: a sensitive technique for accurate evaluation of CpG methylation. Biochem Biophys Res Commun. 2003 Sep. 19; 309(2):305-9.

Zeschnigk M, Bohringer S, Price E A, Onadim Z, Masshofer L, Lohmanr D R. A novel real-time PCR assay for quantitative analysis of methylated alleles (QAMA): analysis of the retinoblastoma locus. Nucleic Acids Res. 2004 Sep. 7; 32(16):e125.

Billerey C, Chopin D, Aubriot-Lorton M H, et al. Frequent FGFR3 mutations in papillary non-invasive bladder (pTa) tumors. AmJPathol 2001; 158:1955-9.

Lotan Y, Roehrborn C G. Sensitivity and specificity of commonly available bladder tumor markers versus cytology: results of a comprehensive literature review and metaanalyses. Urology 2003; 61(1):109-18.

van Oers J M, Lurkin I, van Exsel A J, Nijsen Y, van Rhijn B W, van der Aa M N, Zwarthoff E C. A simple and fast method for the simultaneous detection of nine fibroblast growth factor receptor 3 mutations in bladder cancer and voided urine. Clin Cancer Res. 2005 Nov. 1; 11(21):7743-8.

van Rhijn B W, Vis A N, van der Kwast T H, Kirkels W J, Radvanyi F, Ooms E C, Chopin D K, Boevé E R, Jöbsis A C, Zwarthoff E C. Molecular grading of urothelial cell carcinoma with fibroblast growth factor receptor 3 and MIB-1 is superior to pathologic grade for the prediction of clinical outcome. J Clin Oncol. 2003 May 15; 21(10):1912-21.

van Rhijn B W, van Tilborg A A, Lurkin I, Bonaventure J, de Vries A, Thiery J P, van der Kwast T H, Zwarthoff E C, Radvanyi F. Novel fibroblast growth factor receptor 3 (FGFR3) mutations in bladder cancer previously identified in non-lethal skeletal disorders. Eur J Hum Genet. 2002 December; 10(12):819-24.

Zweig M H, Campbell G. Receiver-operating characteristic (ROC) plots: a fundamental evaluation tool in clinical medicine. Clinical Chemistry 1993, 39, 561-577.

Straub, J. et al., Abstract: A64-AACR Molecular Diagnostics in Cancer Therapeutic Development (2007): Base5, a versatile, highly integrated high-throughput methylation profiling platform for Methylation-Specific PCR based marker identification applied to CRC Renard, I. et al, Abstract: A62-AACR Molecular Diagnostics in Cancer Therapeutic Development (2007): Feasibility of a urine-based DNA methylation assay for early detection of Bladder Cancer The present invention is not to be limited in scope by the specific embodiments described herein. Indeed, various modifications of the invention in addition to those described herein will become apparent to those skilled in the art from the foregoing description and accompanying figures. Such modifications are intended to fall within the scope of the appended claims. Moreover, all embodiments described herein are considered to be broadly applicable and combinable with any and all other consistent embodiments, as appropriate.

Various publications are cited herein, the disclosures of which are incorporated by reference in their entireties.

The invention claimed is:

1. A method comprising:
   (a) treating genomic DNA isolated from bladder cells in a urine sample with a reagent which selectively modifies unmethylated cytosine residues in DNA contained in the sample to produce detectable modified residues but which does not modify methylated cytosine residues;
   (b) amplifying the treated genomic DNA with primers that bind to the promoter region of the TWIST1 gene to produce an amplicon; and
   (c) detecting the amplicon to determine the methylation status of the promoter region of the TWIST1 gene;
   wherein the amplicon is detected by contacting the amplicon with a probe, and:
      (i) the probe comprises the nucleotide sequence of SEQ ID NO:24; or
      (ii) the amplicon comprises the probe binding site for SEQ ID NO:24.

2. The method of claim 1, wherein a stabilizing buffer is added to the urine sample, the stabilizing buffer permitting the urine sample to be stored for a period of up to 72 hours at room temperature without the need for centrifugation of the sample.

3. The method of claim 1, wherein the reagent is a bisulfite reagent.

4. The method of claim 1, wherein the treated genomic DNA is amplified with primers that bind to a methylated sequence in the promoter region of the TWIST1 gene.

5. The method of claim 1, wherein the probe comprises the nucleotide sequence of SEQ ID NO:24.

6. The method of claim 1, wherein the amplicon comprises the probe binding site for SEQ ID NO:24.

7. The method of claim 1, further comprising performing urinary cytology analysis.

8. The method of claim 1, further comprising performing mutation analysis.

9. The method of claim 8, wherein the mutation analysis is FGFR3 gene mutation analysis.

* * * * *